(12) United States Patent
Manku et al.

(10) Patent No.: US 8,318,715 B2
(45) Date of Patent: *Nov. 27, 2012

(54) METHODS OF TREATING HYPERTRIGLYCERIDEMIA

(75) Inventors: Mehar Manku, England (GB); Ian Osterloh, Kent (GB); Pierre Wicker, Mystic, CT (US); Rene Braeckman, Richboro, PA (US); Paresh Soni, Mystic, CT (US)

(73) Assignee: Amarin Pharmaceuticals Ireland Limited, Dublin (IE)

(*) Notice: Subject to any disclaimer, the term of this patent is extended or adjusted under 35 U.S.C. 154(b) by 0 days.

This patent is subject to a terminal disclaimer.

(21) Appl. No.: 13/282,145

(22) Filed: Oct. 26, 2011

(65) Prior Publication Data

US 2012/0093924 A1  Apr. 19, 2012

Related U.S. Application Data

(63) Continuation of application No. 12/702,889, filed on Feb. 9, 2010.

(60) Provisional application No. 61/151,291, filed on Feb. 10, 2009, provisional application No. 61/173,755, filed on Apr. 29, 2009.

(51) Int. Cl.
*A01N 43/00* (2006.01)
*A01N 37/06* (2006.01)
*A61K 31/33* (2006.01)
*A61K 31/02* (2006.01)
*A61K 9/48* (2006.01)

(52) U.S. Cl. .......... 514/183; 514/549; 424/451

(58) Field of Classification Search ........... 514/183, 514/549; 424/451
See application file for complete search history.

(56) References Cited

U.S. PATENT DOCUMENTS

| | | |
|---|---|---|
| 4,377,526 A | 3/1983 | Fujita et al. |
| 4,526,902 A | 7/1985 | Rubin |
| 4,920,098 A | 4/1990 | Cotter et al. |
| 4,935,243 A | 6/1990 | Borkan et al. |
| 5,013,443 A | 5/1991 | Higashidate et al. |
| 5,116,871 A | 5/1992 | Horrobin et al. |
| 5,178,873 A | 1/1993 | Horrobin et al. |
| 5,198,468 A | 3/1993 | Horrobin |
| 5,215,630 A | 6/1993 | Hata et al. |
| 5,252,333 A | 10/1993 | Horrobin |
| 5,457,130 A | 10/1995 | Tisdale et al. |
| 5,502,077 A | 3/1996 | Breivik et al. |
| 5,567,730 A | 10/1996 | Miyashita et al. |
| 5,589,508 A | 12/1996 | Schlotzer et al. |
| 5,603,959 A | 2/1997 | Horrobin et al. |
| 5,618,558 A | 4/1997 | Horrobin et al. |
| 5,656,667 A | 8/1997 | Breivik et al. |
| 5,698,594 A | 12/1997 | Breivik et al. |
| 5,760,081 A | 6/1998 | Leaf et al. |
| 5,776,978 A | 7/1998 | Bruzzese |
| 5,837,731 A | 11/1998 | Vaddadi |
| 5,840,944 A | 11/1998 | Furihata et al. |
| 5,888,541 A | 3/1999 | Horrobin et al. |
| 6,069,168 A | 5/2000 | Horrobin et al. |
| 6,193,999 B1 | 2/2001 | Gennadios |
| 6,331,568 B1 | 12/2001 | Horrobin |
| 6,368,621 B1 | 4/2002 | Engel et al. |
| 6,384,077 B1 | 5/2002 | Peet |
| 6,531,150 B1 | 3/2003 | Sunohara et al. |
| 6,555,700 B1 | 4/2003 | Horrobin et al. |
| 6,689,812 B2 | 2/2004 | Peet |
| 7,119,118 B2 | 10/2006 | Peet |
| 7,498,359 B2 * | 3/2009 | Yokoyama et al. ........... 514/529 |
| 2002/0016312 A1 | 2/2002 | Seed et al. |
| 2002/0055539 A1 | 5/2002 | Bockow et al. |
| 2002/0077361 A1 | 6/2002 | Peet |
| 2002/0183389 A1 | 12/2002 | Peet |
| 2002/0193439 A1 | 12/2002 | Peet |
| 2002/0198177 A1 | 12/2002 | Horrobin et al. |
| 2003/0100610 A1 | 5/2003 | Shibuya et al. |
| 2003/0104048 A1 | 6/2003 | Patel et al. |
| 2003/0166614 A1 | 9/2003 | Harrison |
| 2004/0077723 A1 | 4/2004 | Granata |
| 2004/0162348 A1 | 8/2004 | Peet |
| 2006/0134178 A1 | 6/2006 | Ooisaki et al. |
| 2006/0135610 A1 | 6/2006 | Bortz et al. |
| 2006/0141022 A1 | 6/2006 | Kawamura et al. |
| 2006/0142390 A1 | 6/2006 | Manku et al. |
| 2006/0211762 A1 | 9/2006 | Rongen |
| 2006/0217356 A1 | 9/2006 | Wright et al. |
| 2006/0252833 A1 | 11/2006 | Peet |
| 2007/0104779 A1 | 5/2007 | Rongen et al. |
| 2007/0105954 A1 | 5/2007 | Puri |
| 2007/0141138 A1 | 6/2007 | Feuerstein et al. |
| 2007/0191467 A1 | 8/2007 | Rongen et al. |
| 2008/0125490 A1 | 5/2008 | Svensson et al. |
| 2008/0200547 A1 | 8/2008 | Peet |
| 2009/0012167 A1 | 1/2009 | Rongen et al. |
| 2009/0304784 A1 | 12/2009 | Mane et al. |
| 2011/0034555 A1 | 2/2011 | Osterloh et al. |
| 2011/0288171 A1 | 11/2011 | Manku et al. |

FOREIGN PATENT DOCUMENTS

EP  0 302 482  2/1989

(Continued)

OTHER PUBLICATIONS

Katayama et. al. (Prog. Med. (2001) 21:457-467).*

(Continued)

*Primary Examiner* — Marcos Sznaidman
(74) *Attorney, Agent, or Firm* — K&L Gates LLP

(57) ABSTRACT

In various embodiments, the present invention provides methods of treating and/or preventing cardiovascular-related disease and, in particular, a method of blood lipid therapy comprising administering to a subject in need thereof a pharmaceutical composition comprising eicosapentaenoic acid or a derivative thereof.

19 Claims, No Drawings

FOREIGN PATENT DOCUMENTS

| | | |
|---|---|---|
| EP | 0 460 917 | 12/1991 |
| EP | 0 606 012 | 7/1994 |
| EP | 0 610 506 | 8/1994 |
| EP | 1 296 670 | 4/2003 |
| EP | 1 157 692 B1 | 10/2005 |
| EP | 1 743 644 | 1/2007 |
| EP | 2 022 495 | 2/2011 |
| FR | 2 635 263 | 2/2009 |
| GB | 2 148 713 | 6/1985 |
| GB | 2 221 843 | 2/1990 |
| GB | 2 229 363 | 9/1990 |
| GB | 9 901 809.5 | 1/1999 |
| HU | 0200686 | 2/2002 |
| JP | 04 182426 | 6/1992 |
| WO | 90/04391 | 5/1990 |
| WO | 92/21335 | 12/1992 |
| WO | 94/28891 | 12/1994 |
| WO | 97/39759 | 10/1997 |
| WO | 98/16216 | 4/1998 |
| WO | 99/29316 | 6/1999 |
| WO | 01/15552 | 3/2001 |
| WO | 02/02105 | 1/2002 |
| WO | 02/058793 | 8/2002 |
| WO | 02/089787 | 11/2002 |
| WO | 02/096408 | 12/2002 |
| WO | 03/068216 | 8/2003 |
| WO | 2004/078166 | 9/2004 |
| WO | 2007/017240 | 2/2007 |
| WO | 2007/075841 | 7/2007 |
| WO | 2007/128801 | 11/2007 |
| WO | 2007/142118 | 12/2007 |
| WO | 2008/004900 | 1/2008 |
| WO | 2008/106787 | 9/2008 |

OTHER PUBLICATIONS

Mori et. al. (Mori 1, Am. J. Clin. Nutr. (2000) 71:1085-1094).*
Okumura et. al. (The American Journal of medical Sciences (2002) 324:247-253).*
Hayashi et. al. (Current Therapeutic research (1995) 56:24-31).*
Grimsgaard et. al. (Am. J. Clin. Nutr. (1997) 66:649-659).*
Mori et. al. (Mori 2, Curr. Opinion Clin. Nutr. Metab. Care (2006) 9:95-104).*
Saito (Atherosclerosis (2008) 200:135-140).*
Aarsland, et al., "On the Effect of Peroximsomal β-Oxidation and Carnitine Palmitoyltransferase Activity by Eicosapentaenoic Aid in Live and Heart of Rats." Lipids, 25:546-548, (1990).
Aas, V., et al., "Eicosapentaenoic acid (20:5 n-3) increases fatty acid and glucose uptake in cultured human skeletal muscle cells." Journal of Lipid Research, 47:366-374 (2006).
Abbey, M., et al., "Effect of fish oil on lipoproteins, lecithin:cholesterol acyltransferase, and lipidtransfer protein activity in humans" Arterioscler. Thromb. Vasc. Biol. 10:85-94 (1990).
Adan, Y, et al., "Effects of docosahexaenoic and eicosapentaenoic acid on lipid metabolism, eicosanoid production, platelet aggregation and atherosclerosis." Biosci. Biotechnol. Biochem. 63(1), 111-119 (1999).
Adan, Y., et al., "Concentration of serum lipids and aortic lesion size in female and male apo E-deficient mice fed docosahexaenoic acid." Biosci. Biotechnol. Biochem. 63(2):309-313 (1999).
Agren, J.J., et al., "Fatty acid composition of erythrocyte, platelet, and serum lipids in strict vegans." Lipids 30:365-369 (1995).
Ait-Said, et al., "Inhibition by eicosapentaenoic acid of IL-1β-induced PGHS-2 expression in human microvascular endothelial cells: involvement of lipoxygenase-derived metabolites and p38 MAPK pathway." Biohimicia et Biophysica Acta, 1631:66-85 (2003).
Alderman, J.D., et al., (1989) Effect of a modified, well-toleratd niacin regimen on serum total cholesterol, high density lipoprotein cholesterol and the cholesterol to high density lipoprotein ratio. Am. J. Cardio, 64: 725-729.A.
Alessandri, J-M., et al., "Estradiol favors the formation of eicosapentaenoic acid (20:5n-3) and n-3 docosapentaenoic acid (22:5n-3) from alpha-linolenic acid (18:3n-3) in SH-SY5Y neuroblastoma cells." Lipids 43:19-28 (2008).

Allred, C., et al., "PPARγ1 as a molecular target of eicosapentaenoic acid in human colon cancer (HT-29) cells." J. Nutr. 138:250-256 (2008).
Ando, M., et al., "Eicosapentanoic acid reduces plasma levels of remnant lipoproteins and prevents in vivo peroxidation of LDL in dialysis patients." J. Am. Soc. Nephrol., 10:2177-2184 (1999).
Ando, Y., et al., "Positional distribution of highly unsaturated fatty acids in triacyl-sn-glycerols of Artemia Nauplii enriched with docosahexaenoic acid ethyl ester." Lipids 36:733-740 (2001).
Andrade, S.E., et al., (1995) Discontinuation of antihyperlipidaemic drugs_do rates reported in clinical trials reflect rates in primary care settings? New Eng. J. Med. 332: 1125-1131.
Angerer, P., et al., "n-3 Polyunsaturated Fatty Acids and the Cardiovascular System", Current Opinion in Lipidology, 11(1):57-63, 2000.
Anil, E., "The Impact of EPA and DHA on Blood Lipids and Lipoprotein Metabolism: Influence of ApoE Genoty[e", Proceedings of the Nutrition Society, 66:60-68, 2007.
Aoki T et al. "Experience of the use of ethyl eicosapentaenoic acid preparation (Epadel) in patients with arteriosclerosis obliterans complicated with diabetes mellitus. A study of the long-term effects on glycemic control and blood lipids," Rinsho to Kenkyu 1993; 70:625-631.
Appelton, K.M., et al., "Effects of n-3 long-chain polyunsaturated fatty acids on depressed mood: systematic review of published trials," Am. J. Clin. Nutr. 84(6):1308-1316 (Dec. 2006).
Arshad, A., et al., "Sudden cardiac death and the role of medical therapy." Progress in Cardiovascular Diseases, vol. 50, No. 6, 420-438, (2008).
Arterburn, L., et al., "Distribution, interconversion, and dose response of n-3 fatty acids in humans." Am J Clin Nutr., 83:1467S-76S (2006).
Asano, M., et al., "Inhibitory effects of ω-3 polyunsaturated fatty acids on receptor-mediated non-selective cation currents in rat A7r5 vascular smooth muscle cells." British Journal of Pharmacology 120:1367-1375, (1997).
Asano, M., et al., "Eicosapentaenoic acid inhibits vasopressin-activated Ca2q influx and cell proliferation in rat aortic smooth muscle cell lines." European Journal of Pharmacology 379:199-209 (1999).
ATP III guidelines, NIH publication No. 01-3305 (2001).
Atsushi, Y., et al., J. Biochem., vol. 122, No. 1, "Acyl-transferases and Transacylases . . . ", pp. 1-16, 1997.
Ayton, et al., "A pilot open case series of Ethyl-EPA supplementation in the treatment of anorexia nervosa," Prostaglandins, Leukotrienes and Essential Fatty Acids 71 (2004) pp. 205-209.
Ayton, et al., "Rapid improvement of severe anorexia nervosa during treatment with ethyl-eicosapentaenoate and micronutrients," European Psychiatry 19 (2004) pp. 317-319.
Ballantyne et al., Influence of low-high density lipoprotein cholesterol and elevated triglyceride on coronary heart disease events and response to simvastatin therapy in 4S, Circulation 2001, 104:3046-3051.
Bang HO, Dyerberg J. "Plasma lipids and Lipoproteins in Greenlandic west coast Eskimos" Acta Med Scand 1972; 192:85-94.
Banga, A., et al., "Adiponectin translation is increased by the PPARγ agonists pioglitazone and ω-3 fatty acids." Am J Physiol Endocrinol Metab 296:480-489 (2009).
Bansal S, Buring JE, Rifai N, Mora S, Sacks FM, Ridker PM, "Fasting Compared With Nonfasting Triglycerides and Risk of Cardiovascular Events in Women," JAMA 2007; 298:309-316.
Basu, A., et al., "Dietary Factors That Promote or Retard Inflammation." Arterioscler. Thromb. Vasc. Biol. 26:995-1001 (2006).
Bays, H., Clinical Overview of Omacor: A Concentrated Formulation of Omega-3 Polyunsaturated Fatty Acids, Am J cardiol 2006:98[suppl]:71i-76i.
Bays HE et al. "Prescription omega-3 fatty acids and their lipid effects: physiologic mechanisms of action and clinical implications," Expert Rev Cardiovasc Ther 2008; 6:391-409.
Bays, H., "Rationale for Prescription Omega-3-Acid Ethyl Ester Therapy for Hypertriglyceridemia: A Primer for Clinicians," Drugs of Today 2008,44(3); 205-246.
Beal, M.F., Annals of Neurology, vol. 38, No. 3, "Aging, Energy, and Oxidative Stress in . . .", pp. 357-366, Sep. 1995.

Belmaker, et al., "Addition of Omega-3 Fatty Acid to Maintenance Medication Treatment for Recurrent Unipolar Depressive Disorder," Am J Psychiatry 2002; 159:477-479.

Belmaker, et al., "Omega-3 Eicosapentaenoic Acid in Bipolar Depression: Report of a Small Open-Label Study," J Clin Psychiatry 2005 66:726-729.

Bénistant, C., et al., "Docosapentaenoic acid (22:5, n-3): metabolism and effect on prostacyclin production in endothelial cells." Prostaglandins, Leukotrienes and Essential Fatty Acids, 55(4):287-292, (1996).

Betteridge, D.J., "Diabetic dyslipidaemia: past, present and future." Practical Diabetes Int, 21(2): 78-85. (2004).

Black, K.L., et al., "Effect of intravenous eicosapentaenoic acid on cerebral blood flow, edema, and brain prostaglandins in ischemic gerbils", Prostaglandins (1984), 28(4), pp. 545-546.

Blankenhorn, D.H., et al., (1987) Beneficial effects of combined colestipol-naicin therapy on coronary atheroscherosis and coronary venous bypass grafts. JAMA 257: 3233-3240.

Block, R. C., et al., "EPA and DHA in blood cell membranes from acute coronary syndrome patients and controls." Atherosclerosis, 197(2):821-828 (2007).

Blumenthal (Advanced Studies in Medicine (2002) 2:148-157).

Bonaa, KH et al., Docosahexaenoic and Eicosapentaenoic acids in plasma phospholipids are divergently associated with high density lipoprotein in humans, Arterioscler. Thromb. Vasc. Biol. 1992;12;675-681.

Bousserouel, S., et al., "Different effects of n-6 and n-3 polyunsaturated fatty acids on the activation of rat smooth muscle cells by interleukin-1β." J. Lipid Res. 44:601-611 (2003).

Bousserouel, S., et al., "Modulation of cyclin D1 and early growth response factor-1 gene expression in interleukin-1β-treated rat smooth muscle cells by n-6 and n-3 polyunsaturated fatty acids." Eur. J. Biochem. 271:4462-4473 (2004).

Brady, L., et al., Increased n-6 polyunsaturated fatty acids do not attenuate the effects of long-chain n-3 polyunsaturated fatty acids on insulin sensitivity or triacylglycerol reduction in Indian Asians. Am J Clin Nutr 79:983-91(2004).

Breslow, J., "n-3 Fatty acids and cardiovascular disease." Am J Clin Nutr., 83:1477S-82S (2006).

Brossard, N., et al., "Retroconversion and metabolism of [13C]22:6n-3 in humans and rats after intake of a single dose of [13C]22:6n-3-3-triacyylglycerols." Am. J. Clin. Nutr. 64:577-86 (1996).

Brouwer, I.A., et al., "Effect of fish oil on ventricular tachyarrhythmia and death in patients with implantable cardioverter defibrillators." JAMA. 295(22):2613-2619 (2006).

Brown, G., et al., (1990) Regression of coronary artery-disease as a result of intensive lipid-lowering therapy in men with high levels of apolipoprotein B., N. Engl. J. Med. 323: 1289-1298.

Brown, A. J., et al., "Persistent changes in the fatty acid composition of erythrocyte membranes after moderate intake of n-3 polyunsaturated fatty acids: study design and implications." Am.J. Clin. Nutri. 54:668-73(1991).

Brown, A. J., et al., "Administration of n-3 Fatty Acids in the Diets of Rats or Directly to Hepatocyte Cultures Results in Different Effects on Hepatocellular ApoB Metabolism and Secretion." Arterioscler. Thromb. Vasc. Biol. 19:106-114 (1999).

Brown et al., Simvastatin and Niacin, Antioxidant Vitamins, or the Combination for the Prevention of Coronary Disease, N. Engl J Med, vol. 345, No. 22, Nov. 29, 2001.

Bryhn, M., et al., "The bioavailability and pharmacodynamics of different concentrations of omega-3 acid ethyl esters." Prostaglandins, Leukotrienes and Essential Fatty Acids 75:19-24 (2006).

Budavari, S., Editor, The Merck Index, 1989, Merck & Co., Inc., Rahway, N.J., entry 2417 on p. 379 and 4511 on p. 725.

Bunting, et al., "Depression in Parkinson's Disease", J. Neurosci Nurs. Jun. 1991; 23(3):158-164, (Abstract Only).

Burdge, G.C., et al., "Eicosapentaenoic and docosapentaenoic acids are the principal products of a-linolenic acid metabolism in young men." British Journal of Nutrition 88:355-363 (2002).

Burdge, G.C., et al., "Lack of effect of meal fatty acid composition on postprandial lipid, glucose and insulin responses in men and women aged 50-65 years consuming their habitual diets." British Journal of Nutrition, 96:489-500 (2006).

Burdge, G.C., et al., "The effect of altering the 20:5n-3 and 22:6n-3 content of a meal on the postprandial incorporation of n-3 polyunsaturated fatty acids into plasma triacylglycerol and non-esterified fatty acids in humans." Prostaglandins, Leukotrienes and Essential Fatty Acids 77:59-65 (2007).

Burr, M. L., et al., "Effects of changes in fat, fish and fibre intakes on death and myocardial reinfarction: Diet and reinfarction trial." The Lancet, Sep. 30, 1989; 2(8666):757-61.

Calibresi, L., et al., "Omacor in familial combined hyperlipidemia: effects on lipids and low density lipoprotein subclasses." Atherosclerosis 148:387-396 (2000).

Canner, P.L., et al., (1986) Fifteen year mortality in Coronary Drug Project patients: long-term benefit with niacin, J. Am. Coll. Cardiol. 8. 1245-1255.

Cao, Y., et al., Genomics, vol. 49, "Cloning, Expression, and Chromosomal Localization of Human Long-Chain Fatty Acid CoA Ligase 4 (FACL4)," pp. 327-330, 1998.

Cao, J., et al., "Incorporation and Clearance of Omega-3 Fatty Acids in Erythrocyte Membranes and Plasma Phospholipids." Clinical Chemistry 52(12):2265-2272 (2006).

Capuzzi, et al. "Efficacy and Safety of an Extended-Release Niacin (Niaspan): A Long-Term Study," Am J Cardiol 1998;82:74U-81U.

Carlson, L.A. & Rosenhamer G. (1988). Reduction of mortaility in the Stockholm Ischaemic Heart Disease Secondary Prevention Study by combined treatment with clofibrate and nicotinic acid. Acta Med. Scand. 223, 405-418.

Carlson, L.A., Nicotinic acid: the broad-spectrum lipid drug. A 50$^{th}$ anniversary review, Journal of Internal Medicine, 2005: 258: 94-114.

Carrero et al., "Intake of Fish Oil, Oleic Acid, Folic Acid, and Vitamins B-6 and E for 1 Year Decreases Plasma C-Reactive Protein and Reduces Coronary Heart Disease Risk Factors in Male Patients in a Cardiac Rehabilitation Program", pp. 384-390.

Carroll, D. N., et al., "Evidence for the Cardioprotective Effects of Omega-3 Fatty Acids." Ann Pharmacother., 36:1950-6 (2002).

Cazzola, R., et al., "Age- and dose-dependent effects of an eicosapentaenoic acid-rich oil on cardiovascular risk factors in healthy male subjects." Atherosclerosis 193:159-167 (2007).

Center for Drug Evaluation and Research. Omacor (Lovaza) Medical Reviews 2004 (last accessed May 29, 2008 at http://www.fda.gov/cder/foi/nda/2004/21654_Omacor_Medr.pdf).

Chan et al., "Effect of Atorvastatin and Fish Oil on Plasma High-Sensitivity C-Reactive Protein Concentrations in Individuals with Visceral Obesity", Clin. Chem., vol. 48, pp. 877-883 (2002).

Chan, D.C., et al., "Randomized controlled trial of the effect of n-3 fatty acid supplementation on the metabolism of apolipoprotein B-100 and chylomicron remnants in men with visceral obesity." Am J Clin Nutr 77:300-7 (2003).

Chemical Book, Eicosapentaenoic acid ethyl ester, copyright 2010, printed Jun. 16, 2011 from www.chemicalbook.com.

Chen, H., et al., "Eicosapentanoic acid inhibits hypoxia-reoxygenation-induced injury by attenuating upregulation of MMP-1 in adult rat myocytes." Cardiovascular Research 59:7-13 (2003).

Chen, H., et al., "EPA and DHA attenuate ox-LDL-induced expression of adhesion molecules in human coronary artery endothelial cells via protein kinase B pathway." Journal of Molecular and Cellular Cardiology 35:769-775 (2003).

Chen, I.S., et al., "In vitro clearance of chylomicron triglycerides containing (ω-3) eicosapentaenoate." Atherosclerosis, 65:193-198 (1987).

Childs, M.T., et al., "Divergent lipoprotein Responses to Fish Oils With Various Ratios of Eicosapentaenoic Acid and Docasahexaenoic Acid", American Society for Clinical Nutrition, 52:632-9, 1990.

Christensen, J. H., et al., "Effect of fish oil on heart rate variability in survivors of myocardial infarction: a double blind randomised controlled trial." BMJ, 312:677-678 (1996).

Christensen, M.S., et al., "Intestinal absorption and lymphatic transport of eicosapentaenoic (EPA), docosahexaenoic (DHA), and decanoic acids: dependence on intramolecular triacyiglycerol structure." Am J Clin Nutr 61:56-61 (1995).

Cleland, L.G., et al., "A Biomarker of n-3 compliance in patients taking fish oil for rheumatoid arthritis." Lipids 38:419-424 (2003).
Colhoun, H. M., et al., "Primary prevention of cardiovascular disease with atorvastatin in type 2 diabetes in the Collaborative Atorvastatin Diabetes Study (CARDS): multicentre randomised placebo-controlled trial." Lancet 364: 685-9 (2004).
Collins, N., et al., "Differences between Dietary Supplement and Prescription Drug Omega-3 Fatty Acid Formulations: A Legislative and Regulatory Perspective." Journal of the American College of Nutrition, 27 (6):659-666 (2008).
Conklin, S. M., et al., "Serum ω-3 fatty acids are associated with variation in mood, personality and behavior in hypercholesterolemic community volunteers." Psychiatry Research 152: 1-10 (2007).
Connor, W.E., "Importance of n-3 Fatty Acids in Health and Disease", Am. J. Clin. Nutr., 71(1(S)):171S-175S, 2000.
Contacos et al. Effect of pravastatin and omega-3 fatty acids on plasma lipids and lipoproteins in patients with combined hyperlipidemia, pp. 1755-1762, 1993.
Criqui, M., "Triglycerides and Coronary Heart Disease Revisited (Again)," Sep. 18, 2007, vol. 147 No. 6, pp. 425-427.
Crowe, F. L., et al., "Serum phospholipid n-3 long-chain polyunsaturated fatty acids and physical and mental health in a population-based survey of New Zealand adolescents and adults." Am J Clin Nutr 86:1278-85 (2007).
Daggy, B., et al., Dietary fish oil decreases VLDL production rates. Biochimica et Biophysics Acta 920: 293-300 (1987).
Das, U.N., Essential fatty acids as possible mediators of the actions of statins. Prostaglandins, Leukotrienes and Essential FattyAcids 65(1):37-40, (2001).
Davidson MH. (2006). "Mechanisms for the hypotriglyceridemic effect of marine omega-3 fatty acids." Am J Cardiol 98(4A):27i-33i.
Davidson MH, Stein EA, Bays HE et al. "Efficacy and tolerability of adding prescription omega-3 fatty acids 4 g/d to simvastatin 40 mg/d in hypertriglyceridemic patients: an 8-week, randomized, double-blind, placebo-controlled study," Clin Ther 2007; 29:1354-1367.
De Caterina, R., et al., "The Omega-3 fatty acid docosahexaenoate reduces cytokine-induced expression of proatherogenic and proinflammatory proteins in human endothelial cells." Arterioscler. Thromb. Vasc. Biol. 14:1829-1836 (1994).
De Caterina, R, et al., "Control of Endothelial Leukocyte Adhesion Molecules by Fatty Acids." Lipids, vol. 31:S57-S63 (1996).
Deckelbaum R. J., et al., "Conclusions and recommendations from the symposium, Beyond Cholesterol: Prevention and Treatment of Coronary Heart Disease with n-3 Fatty Acids." Am J Clin Nutr 87:2010S-12S (2008).
Dewailly, E., et al., "n-3 Fatty acids and cardiovascular disease risk factors among the Inuit of Nunavik." Am J Clin Nutr 74:464-73 (2001).
Diagnostic and Statistical Manual of Mental Disorders, 4.sup.th. Ed, published by the American Psychiatric Assoc., pp. 285-286.
Diagnostic and Statistical Manual of Mental Disorders, 4.sup.th. Ed.text revision, published by the American Psychiatric Assoc., pp. 154-163, and 369-381.
Dijan, P., et al., Proc. Natl. Acad. Sci., vol. 93, "Codon repeats in genes associated . . .", pp. 417-421, Jan. 1996.
Dijk, J. M., et al., "Carotid intima—media thickness and the risk of new vascular events in patients with manifest atherosclerotic disease: the SMART study." European Heart Journal 27:1971-1978 (2006).
Dodin, S., et al., "Flaxseed on cardiovascular disease markers in healthy menopausal women: a randomized, double-blind, placebo-controlled trial." Nutrition 24:23-30 (2008).
Dolecek, D.A., "Epidemiological Evidence of Relationships Between Dietary Polyunsaturated Fatty Acids and Morality in the Multiple Risk Factor Intervention Trial", Society of Experimental Biology and Medicine, 200(2):177-182, 1991.
Dullenmeijer, C., et al., "n-3 Fatty acid proportions in plasma and cognitive performance in older adults." Am J Clin Nutr 86:1479-85 (2007).
Duncan, R. E., et al., "Regulation of HMG-CoA reductase in MCF-7 cells by genistein, EPA, and DHA, alone and in combination with mevastatin." Cancer Letters 224:221-228 (2005).
Durrington PN et al. "An omega-3 poly unsaturated fatty acid concentrate administered for one year decreased triglycerides in simvastatin treated patients with coronary heart disease and persistent Hypertriglyceridemia," Heart 2001; 85:544-48.
Dwyer, J. H., et al., "Arachidonate 5-Lipoxygenase Promoter Genotype, Dietary Arachidonic Acid, and Atherosclerosis." N. Engl. J. Med., 350:1 (2004).
Dyerberg, J., et al., "Marine Oils and Thrombogenesis." Prog. Lipid Res. 21:255-269 (1982).
Eisenberg S, Bilheimer DW, Levy RI, Lindgren FT. "On the metabolic conversion of human plasma very low density lipoprotein to low density lipoprotein," Biochim Biophys Acta 1973; 326:361-77.
Eisenberg S, Rachmilewitz D. "Metabolism of rat plasma very low density lipoprotein. I. Fate in circulation of the whole lipoprotein," Biochim Biophys Acta 1973; 326:378-90.
Elam et al., Effect of Niacin on Lipid and Pipoprotein Levels and Glycemic Control in Patients With Diabetes and Peripheral Arterial Disease:Tthe ADMIT Study: A Randomized Trial, JAMA, 2000;284(10); 1263-1270.
El-Sohemy, A., et. al., "Regulation of Mevalonate Synthesis in Low Density Lipoprotein Receptor Knockout Mice Fed n-3 or n-6 Polyunsaturated Fatty Acids." Lipids, 34 (10): 1037-43 (1999).
Engler, et al., "Docosahexaenoic acid restores endothelial function in children with hyperlipidemia: results from the EARLY Study." International Journal of Clinical Pharmacology and Therapeutics, vol. 42—NO. Dec. 2004 (672-679).
Engler, M.B., et al., "Mechanisms of vasorelaxation induced by eicosapentaenoic acid (20:5n-3) in WKY rat aorta." British Journal of Pharmacology 131:1793-1799 (2000).
Engler, M.M., et al., "The effects of a diet rich in docosahexaenoic acid on organ and vascular fatty acid composition in spontaneously hypertensive rats." Prostaglandins, Leukotrienes and Essential Fatty Acids 61(5):289-295 (1999).
Faggin, E., et al., "Fish Oil Supplementation Prevents Neointima Formation in Nonhypercholesterolemic Balloon-Injured Rabbit Carotid Artery by Reducing Medial and Adventitial Cell Activation." Arterioscler. Thromb. Vasc. Biol., 20:152-163 (2000).
Fer, M., et al., "Metabolism of eicosapentaenoic and docosahexaenoic acids by recombinant human cytochromes P450." Archives of Biochemistry and Biophysics 471:116-125 (2008).
Ferns, G., et al., "Investigation and management of hypertriglyceridaemia." J. Clin. Pathol. 61:1174-1183 (2008).
Finnen, M.J., et al., Biochemical Society Trans., "Purification and characterization . . .", p. 19, 1991.
Fischer, R., et al., "Dietary n-3 polyunsaturated fatty acids and direct renin inhibition improve electrical remodeling in a model of high human renin hypertension." Hypertension 51:540-546 (2008).
Flaten, H., et al., "Fish-oil concentrate: effects on variables related to cardiovascular disease." Am. J. Clin. Nutr. 52:300-306 (1990).
Ford, E.S. et al., "Hypertriglyceridemia and Its Pharmacologic Treatment Among US Adults." Arch, Intern. Med., 169(6): 572-78 (2009).
Frick, M.H., et al., (1987) Helsinki Heart Study Primary prevention trial with gemfibrozil in middle-aged men and dyslipidaemia, afety of treatment, changes in risk factors and incidence of coronary heat disease. N. Eng. J. Med. 317: 1237-1245.
Friedman, A. N., et al., "Fish Consumption and Omega-3 Fatty Acid Status and Determinants in Long-Term Hemodialysis." Amer. J. Kidney Diseases, 47(6):1064-1071 (2006).
Frøyland, L., et al., "Hypotriacylglycerolemic component of fish oil." Prostaglandins, Leukotrienes and Essential Fatty Acids 57 (4 & 5):387-388 (1997).
Garg et al., "Niacin treatment increases plasma homocyst(e)ine levels," Am Heart J 1999;138:1082-7.
Garnett, WR, Am J Health-Sys Pharm vol. 52 (1995); 1639-1645.
Genest, J.J., et al., (1992) Familial lipoprotein disorders in patients with premature coronary artery disease, Circulation. 85: 2025-2033.
Geppert, et al. "Microalgal docosahexaenoic acid decreases plasma triacylglycerol in normolipidaemic vegetarians: a randomized trial." British Journal of Nutrition (2006), 95, 779-786.
Gillies, et al. "Effect of a Novel Eicosapentaenoic Acid-Rich Oil on Serum Cholesterol in Man," DuPont 2010.
Ginsberg HN. "Hypertriglyceridemia: new insights and new approaches to pharmacologic therapy," Am J Cardiol 2001; 87:1174-1180.

GISSI—Prevenzione Investigators, "Dietary Supplementation with n-3 Polyunsaturated Fatty Acids and Vitamin E after Myocardial Infarction: Results of the GISSI—Prevenzione Trial", The Lancet, 354:447-455, Aug. 7, 1999.

Glod, "Recent Advances in the Pharmacacotherapy of Major Depression", Arch. Psychiatr. Nurs. Dec. 1996: 10(6):355-364. (Abstract Only).

Goldberg, A C: "Combination therapy of dyslipidemia," Current Treatment Options in Cardiovascular Medicine 200708 GB, vol. 9, No. 4, Aug. 2007,pp. 249-258.

Gordon, D.J., et al., (189) High density lipoprotein cholesterol and cardiovascular disease: four prospective American studies. Circulation, 79: 8-15.

Gorriz, JL (1995) "Rhabdomyolysis and Acute Renal Failure Associated with Bezafibrate Treatment," Nephrol Dial Transplant 10(12):2371-2372.

Gorriz JL et al. (1996) Rhabdomyolysis and Acute Renal Failure Associated with Gemfibrozil Therapy,: Nephron 74(2): 437-438.

Goto, Y., et al., "Clinical Pharmacological Trial of Ethyl Icosapentate (MND-21)—Dose Finding Study." Journal of Clinical Therapeutic & Medicines 8:1293-309 (1992).

Grenyer, Brin F.S., et al., "Fish Oil Supplementation in the Treatment of Major Depression: A Randomised Double-Blind Placebo-Controlled Trial" Progress in Neuro-Psychopharmacology & Biological Psychiatry 31:1393-1396 (2007).

Griffin, M.D., et al., "Effects of altering the ratio of dietary n-6 to n-3 fatty acids on insulin sensitivity, lipoprotein size, and postprandial lipemia in men and postmenopausal women aged 45-70 y: the OPTILIP Study." Am J Clin Nutr 84:1290-8 (2006).

Grimsgaard, S., et al., "Highly purified eicosapentaenoic acid and docosahexaenoic acid in humans have similar triacylglycerol-lowering effects but divergent effects on serum fatty acids" Am. J. Clin. Nutr., 66:649-59, 1997.

Grimsgaard, S., et al., "Effects of Highly Purified Eicosapentaenoic Acid and Docosahexaenoic Acid on Hemodynamics in Humans" American Society for Clinical Nutrition, 68:52-9, 1998.

Grundy et al., Efficacy, Safety, and Tolerability of Once-Daily Niacin for the Treatment of Dyslipidemia Associated with Type 2 Diabetes, Arch Intern Med. 2002;162:1568-1572.

Guallar, E., et al., "Omega-3 fatty acids in adipose tissue and risk of myocardial infarction—The EURAMIC study." Arterioscler. Thromb. Vasc. Biol., 19:1111-1118 (1999).

Guillot, et al., "Increasing intakes of the long-chain ω-3 docosahexaenoic acid: effects on platelet functions and redox status in healthy men," The FASEV Journal, vol. 23, Sep. 2009, pp. 2909-2916.

Guizy, M., et al., "ω-3 and ω-6 Polyunsaturated fatty acids block HERG channels." Am J Physiol Cell Physiol 289:C1251-C1260 (2005).

Hall, W. L., et al., "A high-fat meal enriched with eicosapentaenoic acid reduces postprandial arterial stiffness measured by digital volume pulse analysis in healthy men." J. Nutr. 138: 287-291 (2008).

Hamazaki et al., "Effects of Orally Administered Ethyl Ester of Eicosapentaenoic Acid (EPA: C20:5, omega-3) on PGI2-Like Substance Production by Rat Aorta" Prostaglandins, Apr. 1982, vol. 23 No. 4, pp. 557-567.

Hamazaki T. et al., "Reduction of microalbuminuria in diabetics by Eicosapentaenoic acid ethyl ester" Lipids. 25 (9):542-5 (Sep. 1990).

Hamazaki, T., et al., "Docosahexaenoic Acid-Rich Fish Oil Does Not Affect Serum Lipid Concentrations of Normolipidemic Young Adults", American Institute of Nutrition, 126(11):2784-2789, Nov. 1996.

Han, J. J., et al., "Enhancement of both reaction yield and rate of synthesis of structured triacylglycerol containing eicosapentaenoic acid under vacuum with water activity control." Lipids 34:989-995 (1999).

Hanasaki, K., et al., "Potent modification of low density lipoprotein by group X secretory phospholipase A2 is linked to macrophage foam cell formation." J. Biol. Chem. 277(32):29116-24 (2002).

Hansen, J.B., et al., "Effects of highly purified eicosapentaenoic acid and docosahexaenoic acid on fatty acid absorption, incorporation into serum phospholipids and postprandial triglyeridemia." Lipids 33:131-38 (1998).

Harkonarson, H., et al., "Effects of a 5-lipoxygenase-activating protein inhibitor on biomarkers associated with risk of myocardial infarction—a randomized trial." JAMA, 293(8):2245-56 (2005).

Harris, W. S., "Fish oils and plasma lipid and lipoprotein metabolism in humans: a critical review." J Lipid Res. 30:785-807 (1989).

Harris, W. S., et al., "Influence of n-3 fatty acid supplementation on the endogenous activities of plasma lipases." Am. J. Clin. Nutr. 66:254-60 (1997).

Harris, W. S., et al., "n-3 Fatty acids and urinary excretion of nitric oxide metabolites in humans." Am. J. Clin. Nutr., 65:459-64 (1997).

Harris, W.S., "n-3 Fatty acids and serum lipoproteins: human studies." Am J Clin Nutr 65:1645S-54S (1997).

Harris, W. S. et al. "Safety and efficacy of Omacor in severe hypertriglyceridemia," Journal of Cardiovascular Risk 1997, 4:385-391.

Harris, W.S., "n-3 Fatty acids and human lipoprotein metabolism: an update." Lipids 34:S257-S258 (1999).

Harris, W.S., "Omega-3 fatty acids in cardiac biopsies from heart transplantation patients." Circulation 110;1645-1649 (2004).

Harris, W.S., et al., "Stearidonic acid increases the red blood cell and heart eicosapentaenoic acid content in dogs." Lipids 42:325-333 (2007).

Harris, W.S., et al., "Tissue n-3 and n-6 fatty acids and risk for coronary heart disease events." Atherosclerosis 193:1-10 (2007).

Harris, W.S., "Expert opinion: omega-3 fatty acids and bleeding—cause for concern?" The American Journal of Cardiology 99(6A): 45C-46C (2007).

Harris, W.S., et al., "Comparison of the effects of fish and fish-oil capsules on the n-3 fatty acid content of blood cells and plasma phospholipids." Am J Clin Nutr 86:1621-5 (2007).

Harris, W.S., et al., "Omega-3 fatty acids and coronary heart disease risk: Clinical and mechanistic perspectives." Atherosclerosis 197:12-24 (2008).

Harris, W. S., "The omega-3 index as a risk factor for coronary heart disease." Am J Clin Nutr 87:1997S-2002S (2008).

Hawthorne, et al., "High dose eicosapentaenoic acid ethyl ester: effects on lipids and neutrophil leukotriene production in normal volunteers." Br. J. Clin. Pharmac. (1990), 30, 187-194.

Hayashi et al., Decreases in Plasma Lipid Content and Thrombotic Activity by Ethyl Icosapentate Purified from Fish Oiles, Current Therapeutic Research, vol. 56, No. 1, Jan. 1995, pp. 24-31.

Hibbeln, J. R., et al., "Healthy intakes of n-3 and n-6 fatty acids: estimations considering worldwide diversity." Am J Clin Nutr. 83:1483S-93S (2006).

Hilpert, K.F., et al., "Postprandial effect of n-3 polyunsaturated fatty acids on apolipoprotein B-containing lipoproteins and vascular reactivity in type 2 diabetes." Am J Clin Nutr 85:369-76 (2007).

Hirafuji, M., et al., "Docosahexaenoic acid potentiates interleukin-1b induction of nitric oxide synthase through mechanism involving p44/42 MAPK activation in rat vascular smooth muscle cells." British Journal of Pharmacology 136:613-619 (2002).

Hirai, A., et al., (1982). The effects of the oral administration of fish oil concentrate on the release and the metabolism of [$^{14}$C] arachidonic acid and [$^{14}$C] eicosapentaenoic acid by human platelets. Thromb. Res. 28: 285-298.

Holmeide, A. K., et al., "Oxidative degradation of eicosapentaenoic acid into polyunsaturated aldehydes." Tetrahedron 59:7157-7162 (2003).

Holub, B.J., PhD, "Fish Oils and Cardiovascular Disease", Canadian Medical Association Journal, 141(10):1063, Nov. 15, 1989.

Hombeck, M., et al., "Biosynthesis of the algal pheromone fucoserratene by the freshwater diatom Asterionella formosa (Bacillariophyceae)." Tetrahedron 54:11033-11042 (1998).

Hoskins et al., Combination use of statins and omega-3 fatty acids: an emerging therapy for combined hyperlipidemia, pp. 579-591—Abstract only.

Howe, P.R.C., et al., "Equal antithrombotic and triglyceride-lowering effectiveness of eicosapentaenoic acid-rich and docosahexaenoic acid-rich fish oil supplements." Lipids 34:S307-S308 (1999).

Huntington's Diesase Drug Works—The DHA Dilemma http://hd-drugworks.org/index2.php?option=com_content&task=view&id=185&pop=1&pa... Printed on Aug. 22, 2008.

Illingworth et al., "Comparative Effects of Lovastatin and Niacin in Primary Hypercholesterolemia. A Prospective Trial," Arch Intern med. 1994;154:1586-1595.

Inoue, I., et al., "Expression of peroxisome proliferator-activated receptor α(PPARα) in primary cultures of human vascular endothelial cells." Biochem. Biophys. Res. Comm., 246, 370-374 (1998).

Ishida, Y., et al., "α-Lipoic Acid and Insulin Autoimmune Syndrome." Diabeters Care, 30(9): 2240-41 (2007).

Isley, et al., "Pilot study of combined therapy with ω-3 fatty acids and niacin in atherogenic dyslipidemia," Journal of Clinical Lipidology (2007) 1, 211-217.

Jacobson et al. "Hypertriglyceridemia and Cardiovascular Risk Reduction", Clinical Therapeutics, vol. 29 pp. 763-777 (2007).

Jacobson, T. Secondary Prevention of Coronary Artery Disease with Omega-3 Fatty Acids. Am J Cardiol 2006; 98 [suppl]: 61i-70i.

Jacobson, T.A., "Role of n-3 fatty acids in the treatment of hypertriglyceridemia and cardiovascular disease." Am J Clin Nutr 87:1981S-90S (2008).

Jenner, "Presymptomatic Detection of Parkinson's Disease". J Neural Transm Suppl, 1993; 40:23-36. (Abstract only).

Jialal, I., "Editorial: Remnant lipoproteins: measurement and clinical significance." Clinical Chemistry 48(2):217-219 (2002).

Jung, U.J., et al., "n-3 Fatty acids and cardiovascular disease: mechanisms underlying beneficial effects." Am J Clin Nutr 87: 2003S-9S (2008).

Kanayasu, T., et al., "Eicosapentaenoic acid inhibits tube formation of vascular endothelial cells in vitro." Lipids 26:271-276 (1991).

Katan, M. B., et al., "Kinetics of the incorporation of dietary fatty acids into serum cholesteryl esters, erythrocyte membranes, and adipose tissue: an 18-month controlled study." J. Lipid Res. 38: 2012-2022 (1997).

Katayama et al. (Prog. Med.(2001) 21:457-467, translated from Japanese).

Kato, T., et al., "Palmitate impairs and eicosapentaenoate restores insulin secretion through regulation of SREBP-1c in pancreatic islets." Diabetes, 57(9):2382-2392 (2008) (published online May 5, 2008.).

Kawano, H., et al., (2002). Changes in aspects such as the collagenous fiber density and foam cell size of atherosclerotic lesions composed of foam cells, smooth muscle cells and fibrous components in rabbits caused by all-cis 5, 8, 11, 14, 17-icosapentaenoic acid. J. Atheroscler. Thromb. 9: 170-177.

Kawashima, H., et al., "Oral Administration of Dihomo-γ-Linolenic Acid Prevents Development of Atopic Dermatitis in NC/Nga Mice." Lipids 43:37-43 (2008).

Kelley, et al., "Docosahexaenoic acid supplementation improves fasting and postprandial lip profiles in hypertriglyceridemic men." The American Journal of Clinical Nutrition, 2007; 86: 324-333.

Kelley, D. S., et al., "Docosahexaenoic Acid Supplementation Decreases Remnant-Like Particle-Cholesterol and Increases the (n-3) Index in Hypertriglyceridemic Men." J. Nutr. 138: 30-35 (2008).

Kew, S., et al., "Effects of oils rich in eicosapentaenoic and docosahexaenoic acids on immune cell composition and function in healthy humans." Am J Clin Nutr 79:674-81 (2004).

Kimura, F., et al., "Long-term supplementation of docosahexaenoic acid-rich, eicosapentaenoic acid-free microalgal oil in n-3 fatty acid-deficient rat pups." Biosci. Biotechnol. Biochem., 72(2):608-610 (2008).

Kinsella, J.E., et al., "Dietary n-3 polyunsaturated fatty acids and amelioration of cardiovascular disease: possible mechanisms." Am J Clin Nutr 52:1-28 (1990).

Knopp et al., "Contrasting Effects of Unmodified and Time-Release Forms of Niacin on Lipoproteins in Hyperlipidemic Subjects: Clues to Mechanism of Action of Niacin," Northwest Lipid Research Clinic, Department of Medicine, School of Medicine, University of Washington, Seattle, 1985, pp. 642-650.

Kohno, M., et al., "Inhibition by Eicosapentaenoic Acid of Oxidized-LDL- and Lysophosphatidylcholine-Induced Human Coronary Artery Smooth Muscle Cell Production of Endothelin." J. Vasc. Res. 38:379-388 (2001).

Kojima, T,. et al., "Long-term administration of highly purified eicosapentaenoic acid provides improvement of psoriasis." Dermatologica, 182:225-230 (1991).

Kosonen, O., et al., "Inhibition by nitric oxide-releasing compounds of E-selectin expression in and neutrophil adhesion to human endothelial cells." European Journal of Pharmacology 394:149-156 (2000).

Kris-Ehterton, P. M., et al., "Omega-3 Fatty Acids and Cardiovascular Disease—New Recommendations From the American Heart Association." Arterioscler Thromb Vasc Biol. 23:151-152 (2003).

Ku, K., et al., "Beneficial Effects of t-o-3 Fatty Acid Treatment on the Recovery of Cardiac Function After Cold Storage of Hyperlipidemic Rats." Metabolism, 48(10):123-1209 (1999).

Kurabayashi, T., et al., "Eicosapentaenoic acid effect on hyperlipidemia in menopausal Japanese women." Obstet Gynecol 96:521-8 (2000).

Lai et al., Suppression of Niacin-induced Vasodilation withan Antagonist to Prostaglandin $D_2$ Receptor Subtype 1, clinical Pharmacology & Therapeutics, vol. 81, No. 6, Jun. 2007, pp. 849-857.

Laidlaw, M., et al., "Effects of supplementation with fish oil-derived n-3 fatty acids and γ-linolenic acid on circulating plasma lipids and fatty acid profiles in women." Am J Clin Nutr 77:37-42 (2003).

Larsen, L.N., et al., "Heneicosapentaenoate (21:5n-3): Its incorporation into lipids and its effects on arachidonic acid and eicosanoid Synthesis." Lipids 32:707-714 (1997).

Leaf, A., "Historical overview of n3 fatty acids and coronary heart disease." Am J Clin Nutr 87:1978S-80S. (2008).

Lee, J.H., et al., "Omega-3 fatty acids for cardioprotection." Mayo Clin Proc., 83(3):324-332 (2008).

Lee, K.W., et al., "The Role of Omega-3 Fatty Acids in the Secondary Prevention of Cardiovascular Disease", Q J Med, 96:465-480, 2003.

Lemaitre, R.N., et al., "n-3 Polyunsaturated fatty acids, fatal ischemic heart disease, and nonfatal myocardial infarction in older adults: the Cardiovascular Health Study." Am J Clin Nutr 77:319-25 (2003).

Leucht, S., et al., Schizophrenia Research, vol. 35, "Efficacy and extrapyramidal side-effects of the new antipsychotics olanzapine, quetiapine, risperidone, and sertindole compared to conventional antipsychotics and placebo. A meta-analysis of randomized controlled trials", pp. 51-68, 1999.

Leonard, B.E., Fundamentals of Psychopharmacology, pp. 186-187, 1997.

Li, D., et al., "Effect of dietary a-linolenic acid on thrombotic risk factors in vegetarian men." Am J Clin Nutr 69:872-82 (1999).

Li, H., et al., "EPA and DHA reduce LPS-induced inflammation responses in HK-2 cells: Evidence for a PPAR-γ-dependent mechanism." Kidney Int'l. 67:867-74 (2005).

Lin, Pao-Yen, M.D., et al. "A Meta-Analytic Review of Double-Blind, Placebo-Controlled Trials of Antidepressant Efficacy of Omega-3 Fatty Acids", Psychiatry, 1056-1061 (Jul. 2007).

Lin, Y., et al., "Differential effects of eicosapentaenoic acid on glycerolipid and apolipoprotein B metabolism in primary human hepatocytes compared to HepG2 cells and primary rat hepatocytes." Biochimica et Biophysica Acta 1256:88-96 (1995).

Lohmussaar, E., et al., "ALOX5AP Gene and the PDE4D Gene in a Central European Population of Stroke Patients." Stroke, 36:731-736 (2005).

LOVAZA® (omega-3-acid ethyl esters) Capsules, Prescribing information, 12 pgs., © Jun. 2008, GlaxoSmithKline.

Lucas, M., et al., "Ethyl-eicosapentaenoic acid for the treatment of psychological distress and depressive symptoms in middle-aged women: a double-blind, placebo-controlled, randomized clinical trial." Am J Clin Nutr 89:641-51 (2009).

Luria, M. "Effect of Low-Dose Niacin on High-Density Lipoprotein Cholesterol and Total Cholesterol/High-Density Lipoprotein Cholesterol Ratio," Arch Intern Med 1988;148:2493-2495.

Madhavi, N., et al., "Effect of n-6 and n-3 fatty acids on the survival of vincristine sensitive and resistant human cervical carcinoma cells in vitro", Cancer Letters, vol. 84, No. 1, 1994, pp. 31-41.

Madsen, L., et al., "Eicosapentaenoic and Docosahexaenoic Acid Affect Mitochondrial and Peroxisomal Fatty Acid Oxidation in Relation to Substrate Preference." Lipids 34:951-963 (1999).

Maki, PhD, et al., "Lipid Responses to a Dietary Docosahexaenoic Acid Supplement in Men and Women with Below Average Levels of High Density Lipoprotein Cholesterol." Journal of the American College of Nutrition, vol. 24, No. 3, 189-199 (2005).

Mallat, Z., et al., "Protective role of interleukin-10 in atherosclerosis." Circ. Res. 85:e17-e24 (1999).

Mallat, Z., et al., "Apoptosis in the vasculature: mechanisms and functional importance." British Journal of Pharmacology 130:947-962 (2000).

Marangell, L. B., et al., "A Double-Blind, Placebo-Controlled Study of the Omega-3 Fatty Acid Docosahexaenoic Acid in the Treatment of Major Depression" Am J Psychiatry, 160(5):996-998, (May 2003).

Marckmann, P., "Fishing for heart protection." Am J Clin Nutr, 78:1-2 (2003).

Mater, M.K., et al., "Arachidonic acid inhibits lipogenic gene expression in 3T3-L1 adipocytes through a prostanoid pathway." J. Lipid Res. 39:1327-1334 (1998).

Matsumoto, M., et al., "Orally administered eicosapentaenoic acid reduces and stabilizes atherosclerotic lesions in ApoE-deficient mice." Atherosclerosis, 197(2):524-533 (2008).

Matsuzawa, Y., et al., "Effect of Long-Term Administration of Ethyl Icosapentate (MND-21) in Hyperlipaemic Patients," J. Clin Therapeutic & Medicines 1991; 7: 1801-16.

Mayatepek, E., et al., The Lancet, vol. 352, "Leukotriene C4-synthesis deficiency . . . ", pp. 1514-1517, Nov. 7, 1998.

McElroy, S.L., et al., "Clozapine in the Treatment of Psychotic Mood Disorders, Schizoaffective Disorder, and Schizophrenia", Journal of Clinical Psychiatry, vol. 52, No. 10, Oct. 1991, pp. 411-414.

McKenney, James et al., "Role of prescription omega-3 fatty acids in the treatment of Hypertriglyceridemia," Pharmacotherapy, May 2007 LNKD—Pubmed: 17461707, vol. 27, No. 5, pp. 715-728.

McMurchie, E.J., et al., "Incorporation and effects of dietary eicosapentaenoate (20 : 5( n-3)) on plasma and erythrocyte lipids of the marmoset following dietary supplementation with differing levels of linoleic acid." Biochimica et Biophysics Acta, 1045:164-173 (1990).

Menuet, R. et al., "Importance and management of dyslipidemia in the metabolic syndrome," American Journal of the Medical Sciences 200512 US, vol. 33, No. 6, Dec. 2005, pp. 295-302.

Merched, A.J., et al., "Atherosclerosis: evidence for impairment of resolution of vascular inflammation governed by specific lipid mediators." FASEB J. 22:3595-3606 (2008).

Mesa, M., "Effects of oils rich in Eicosapentaenoic and docosahexaenoic acids on the oxidizability and thrombogenicity of low-density lipoprotein," Artherosclerosis 175 (2004) 333-343.

Metcalf, R.G., et al., "Effects of fish-oil supplementation on myocardial fatty acids in humans." Am J Clin Nutr 85:1222-28 (2007).

Metcalf, R.G. et al., "Effect of dietary n-3 polyunsaturated fatty acids on the inducibility of ventricular tachycardia in patients with ischemic cardiomyopathy." Am J Cardiol 101:758-761 (2008).

Meyer, et al., "Dose-Dependent Effects of Docosahexaenoic Acid Supplementation on Blood Lipids in Statin-Treated Hyperlipidaemic Subjects." Lipids (2007) 42:109-115.

Meyers et al., Nicotinic acid induces secretion of prostaglandin $D_2$ in human macrophages: An in vitro model of the niacin flush, Artherosclerosis 192 (2007) 253-258.

Mii, S., et al., "Perioperative use of eicosapentaenoic acid and patency of infrainguinal vein bypass: a retrospective chart review." Curr Ther Res Clin Exp. 68:161-174 (2007).

Miller, M., et al., "Impact of lowering triglycerides on raising HDL-C in hypertriglyceridemic and non-hypertriglyceridemic subjects." International Journal of Cardiology 119:192-195 (2007).

Minihane, A.M., et al., "ApoE polymorphism and fish oil supplementation in subjects with an atherogenic lipoprotein phenotype." Arterioscler. Thromb. Vasc. Biol. 20:1990-1997 (2000).

Mishra, A., et al., "Oxidized omega-3 fatty acids inhibit NF-κB activation via a PPARα-Dependent Pathway." Arterioscler Thromb Vasc Biol. 24:1621-1627 (2004).

Mita, T. et al., Eicosapentaenoic acid reduces the progression of carotid intima-media thickness in patients with type 2 diabetes, Atherosclerosis 191 (2007) 162-167.

Mizota M, Katsuki Y, Mizuguchi K, Endo S, Miyata H, Kojima M, Kanehiro H et al. "Pharmacological studies of eicosapentaenoic acid ethylester (EPA-E) on high cholesterol diet-fed rabbits," Nippon Yakurigaku Zasshi 1988; 91:255-66.

Mizota M, Katsuki Y, Mizuguchi K, Endo S, Miyata H, Kojima M, Kanehiro H et al. "The effects of eicosapentaenoic acid ethylester (EPA-E) on arterial thrombosis in rabbits and vascular lesions in rats," Nippon Yakurigaku Zasshi 1988; 91:81-9.

Mizuguchi K, Yano T, Kojima M, Tanaka Y, Ishibashi M, Masada A, Sato M et al. "Hypolipidemic effect of ethyl all-cis-5,8,11,14,17-eicosapentaenoate (EPA-E) in rats," Jpn J Pharmacol 1992; 59:3307-12.

Mizuguchi, K., et al., "Mechanism of the lipid-lowering effect of ethyl all-cis-5,8,11,14,17- icosapentaenoate." European Journal of Pharmacology, 231:121-127 (1993).

Mizuguchi, K., et al., "Ethyl all-cis-5,8,11,14,17-icosapentaenoate modifies the biochemical properties of rat very low-density lipoprotein." European Journal of Pharmacology, 231:221-227 (1993).

Mori, T., et al., "Docosahexaenoic Acid but Not Eicosapentaenoic Acid Lowers Ambulatory Blood Pressure and Heart Rate in Humans" Hypertension, (Aug. 1999).

Mori, et al., "Purified Eicosapentaenoic and docosahexaenoic acids have differential effects on serum lipids and lipoproteins, LDL particle size, glucose, and insulin in mildly hyperlipidemic men," Am J Cl;in Nutr 2000; 71:1085-1094.

Mori, T. et al., Effect of Eicosapentaenoic acid and docosahexaenoic acid on oxidative stress and inflammatory markers in treated-hypertensive type 2 diabetic subjects, Free Radical Biology & Medicine, vol. 35, No. 7, pp. 772-781, 2003.

Mori TA, Woodman RJ. "The independent effects of eicosapentaenoic acid and docosahexaenoic acid on cardiovascular risk factors in humans," Curr Opin Clin Nutr Metab Care 2006; 9:95-104.

Morita, I., et al., "Effects of purified eicosapentaenoic acid on arachidonic acid metabolism in cultured murine aortic smooth muscle cells, vessel walls and platelets." Lipids 18:42-490 (1983).

Morrow et al., Release of Markedly Increased Quantities of Prostaglandin D2 In Vivo in Humans Following the Administration of Nicotinic Acid, Protaglandins, Aug. 1989, vol. 38, No. 2., pp. 263-274.

Mosher LR et al., "Nicotinic Acid Side Effects and Toxicity: A review," Am J Psychiat. 1970; 126: 1290-1296.

Mostad, LL, et al., "Effects of n-3 fatty acids in subjects with type 2 diabetes: reduction of insulin sensitivity and time-dependent alteration from carbohydrate to fat oxidation." Am J Clin Nutr 84:540-50 (2006).

Mozaffarian, "JELIS, fish oil, and cardiac events," www.thelancet.com vol. 369, Mar. 31, 2001, pp. 1062-1063.

Mozaffarian, D., "Fish and n-3 fatty acids for the prevention of fatal coronary heart disease and sudden cardiac death." Am J Clin Nutr, 87:1991S-6S (2008).

Mozaffarian, D., et al., "Dietary fish and ω-3 fatty acid consumption and heart rate variability in US adults." Circulation, 117:1130-1137 (2008).

Naba, H., et al., "Improving effect of ethyl eicosapentanoate on statin-induced rhabdomyolysis in Eisai hyperbilirubinemic rats." Biochemical and Biophysical Research Communications, 340:215-220 (2006).

Nakamura, et al., "Effects of Eicosapentaenoic Acids on Remnant-like Particles, Cholesterol Concentrations and Plasma Fatty Acid Composition in Patients with Diabetes Mellitus." in vivo 12: 311-314 (1998).

Nakamura, H., et al., "Evaluation of ethyl icosapentate in the treatment of hypercholesterolemia in kidney transplant recipients." Transplantation Proceedings, 30:3047-3048 (1998).

Nakamura, N., et al., "Joint effects of HMG-CoA reductase inhibitors and eicosapentaenoic acids on serum lipid profile and plasma fatty acid concentrations in patients with hyperlipidemia", international Journal of Clinical and Laboratory Research, Springer, Berlin, DE LNKD-DOI: 10.1007/S005990050057, vol. 29, No. 1, Mar. 1, 1999, pp. 22-25.

Nambi, V., et al., "Combination therapy with statins and omega-3 fatty acids." Am J Cardiol 98:34i-38i (2006).

Nasa, et al., "Long-Term Supplementation With Eicosapentaenoic Acid Salvages Cardiomyocytes From Hypoxia/Reoxygenation-Induced Injury in Rats Fed With Fish-Oil-Deprived Diet," Jpn. J. Pharmacol. 77, 137-146 (1998).

Nattel, S., et al., "Atrial remodeling and atrial fibrillation: Mechanisms and implications." Circ Arrhythmia Electrophysiol, 1:62-73 (2008).

Negre-Salvayre, A., et al., "Advanced lipid peroxidation end products in oxidative damage to proteins. Potential role in diseases and therapeutic prospects for the inhibitors." British Journal of Pharmacology 153:6-20 (2008).

Nelson, G. J., et al., "The Effect of Dietary Docosahexaenoic Acid on Plasma Lipoproteins, and Tissue Fatty Acids Composition in Humans", Lipids, AOCS Press, 32(11):1137-1146, 1997.

Nemets, B., "Addition of Omega-3 Fatty Acid to Maintenance Medication Treatment for Recurrent Unipolar Depressive Disorder" Am J Psychiatry, 159(3):477-479 (Mar. 2002).

Nenseter, MS et al., "Effect of dietary supplementation with n-3 polyunsaturated fatty acids on physical properties and metabolism of low density lipoprotein in humans," Arterioscler. Thromb. Vasc. Biol. 1992; 12;369-379.

Nestel, et al., "The n-3 fatty acids eicosapentaenoic acid and docosahexaenoic acid increase systemic arterial compliance in humans," Am J Clin Nutr 2002; 76:326-30.

Nishikawa M. et al., "Effects of Eicosapentaenoic acid (EPA) on prostacyclin production in diabetics. GC/MS analysis of PG12 and PG13 levels" Methods Find Exp Clin Pharmacol. 19(6):429-33 (Jul.-Aug. 1997).

Nobukata, H., et al., "Long-term administration of highly purified eicosapentaenoic acid ethyl ester prevents diabetes and abnormalities of blood coagulation in male WBN/Kob rats." Metabolism, 49(12): 912-919 (2000).

Nobukata, H., et al., "Long-term administration of highly purified eicosapentaenoic acid ethyl ester improves the dysfunction of vascular endothelial and smooth muscle cells in male WBN/Kob rats." Metabolism, 49(12): 1588-1591 (2000).

Nobukata, H., et al., "Age-related changes in coagulation, fibrinolysis, and platelet aggregation in male WBN/Kob rats." Thrombosis Research 98: 507-516 (2000).

Nourooz-Zadeh, J., et al., "Urinary 8-epi-PGF2α and its endogenous β-oxidation products (2,3-dinor and 2,3-dinor-5,6-dihydro) as biomarkers of total body oxidative stress." Biochemical and Biophysical Research Communications 330:731-736 (2005).

Nozaki S. et al., "Effects of purified Eicosapentaenoic acid ethyl ester on plasma lipoproteins in primary hypercholesterolemia" Int J Vitam Nutr Res. 62(3):256-60 (1992).

Obata, et al., (1999) Eicosapentaenoic acid inhibits prostaglandin $D_2$ generation by inhibiting cyclo-oxygenase in cultured human mast cells. Clin. & Experimental Allergy 29: 1129-1135.

O'Donnell, C.J., et al., "Leukocyte telomere length and carotid artery intimal medial thickness—the Framingham heart study." Arteriosclerosis, Thrombosis, and Vascular Biology.28:1165-1171 (2008).

Oh, Robert C et al., Management of Hypertriglyceridemia, American Family Physician, May 1, 2007, LNKD-PUBMED: 17508532, vol. 75, No. 9, pp. 1365-1371.

Okuda, Y., et al., "Long-term effects of eicosapentaenoic acid on diabetic peripheral neuropathy and serum lipids in patients with type II diabetes mellitus." Journal of Diabetes and Its Complications 10:280-287 (1996).

Okuda, Y., et al., (1997) Eicosapentaenoic acid enhances nitric oxide production by cultured human endothelial cells. Biochem. Biophys. Res. Commun. 232: 487-491 (1997).

Okumura, T., et al., "Eicosapentaenoic acid improves endothelial function in hypertriglyceridemic subjects despite increased lipid oxidizability." Am J Med Sci 324(5):247-253 (2002).

Oliw, E.H., et al., "Biosynthesis of prostaglandins from 17(18)epoxy-eicosatetraenoic acid, a cytochrome P-450 metabolite of eicosapentaenoic acid." Biochimica el Biophysica Acta, 1126 (1092) 261-268.

Ona, V.O., et al., Nature, vol. 399, "Inhibition of caspase-1 slows disease progression . . . ", pp. 263-267, May 20, 1999.

Ozawa A, Nakamura E, Jinbo H. Fujita T, Hirai A, Terano T, Hamazaki T et al. "Measurement of higher lipids in the fractions of human red blood cell membranes, blood platelets and plasma, using thin layer chromatography and gas chromatography," Bunseki Kagaku 1983; 32:174-8.

Park, Y., et al., "Omega-3 fatty acid supplementation accelerates chylomicron triglyceride clearance." J. Lipid Res. 44:455-463 (2003).

Pedersen, T., et al., "Randomised trial of cholesterol lowering in 4444 patients with coronary heart disease: the Scandinavian Simvastation Survival Study (4S)", The Lancet, No. 19, 1994, vol. 344, 8934, p. 1383-1389.

Peet, M., et al., Phospholipid Spectrum Disorder in Psychiatry pp. 1-19, 1999.

Peet, M., et al., "A Dose-Ranging Study of the Effects of Ethyl-Eicosapentaenoate in Patients with Ongoing Depression Despite Apparently Adequate Treatment with Standard Drugs", Arch Gen Psychiatry, 59:913-919, (Oct. 2002).

Piccini, Monica, et al., Genomics, vol. 47, "FACL4, a New Gene Encoding Long-Chain Acyl-CoA . . . ", pp. 350-358, 1998.

Pike, N., "Flushing out the role of GPR109A (HM74a) in the clinical efficacy of nicotinic acid," The Journal of Clinical Investigation, vol. 115, No. 12, Dec. 2005, pp. 3400-3403.

Pownall, H.J., et al., "Correlation of serum triglyceride and its reduction by ω-3 fatty acids with lipid transfer activity and the neutral lipid compositions of high-density and low-density lipoproteins." Atherosclerosis 143:285-297 (1999).

Press Release: Amarin Corporation Says Huntington's Disease Drug Failed in Trials, http://www.fiercebiotech.com/node/6607/print (Apr. 24, 2007) Printed on Aug. 22, 2008.

Press Release from Mochida Pharmaceutical Col., Ltd.: Conclusion of Distributorship Agreement Concerning Switch-OTC Drug for Hyperlipidemia Treatment, Epadel, published Apr. 30, 2009.

Puri, B., et al., Archives of General Psychiatry, No. 55, "Sustained remission of positive and . . . ", pp. 188-189, 1998.

Puri, B., et al., "Eicosapentaenoic Acid in Treatment-Resistant Depression Associated with Symptom Remission, Structural Brain Changes and Reduced Neuronal Phospholipid Turnover," Int J Clinical Practice 2001; 55:560-563.

Puri, B.K., et al., "Ethyl-EPA in Huntington Disease: A Double-Blind, Randomized, Placebo-Controlled Trial", Neurology 65:286-292, (2005).

Qi, K., et al., "Omega-3 fatty acid containing diets decrease plasma triglyceride concentrations in mice by reducing endogenous triglyceride synthesis and enhancing the blood clearance of triglyceride-rich particles." Clinical Nutrition 27(8):424-430 (2008).

Raitt, M.H., et al., "Fish oil supplementation and risk of ventricular tachycardia and ventricular fibrillation in patients with implantable defibrillators—a randomized controlled trial." JAMA. 293(23):2884-2891 (2005).

Rambjor, Gro S., et al., "Elcosapentaenoic Acid is Primarily Responsible for Hypotrigylceridemic Effect of Fish Oil in Humans", Fatty Acids and Lipids from Cell Biology to Human Disease: Proceedings of the $2^{nd}$ international Congress of the ISSFAL (Internaitonal Society for the Study of Fatty Acids and Lipids, AOCS Press, 31:S-45-S-49, 1996.

Reiffel, J.A., et al., "Antiarrhythmic effects of omega-3 fatty acids." Am J Cardiol 98:50i-60i (2006).

Riediger, N. D., et al., "A systemic review of the roles of n-3 fatty acids in health and disease." J Am Diet Assoc. 109:668-679. (2009).

Risé, P., et al., "Effects of simvastatin on the metabolism of polyunsaturated fatty acids and on glycerolipid, cholesterol, and de novo lipid synthesis in THP-1 cells." J. Lipid Res. 38:1299-1307 (1997).

Roche, H.M., et al., "Long-chain n-3 polyunsaturated fatty acids and triacylglycerol metabolism in the postprandial state." Lipids 34: S259-S265 (1999).

Roche, H.M., et al., "Effect of long-chain n-3 polyunsaturated fatty acids on fasting and postprandial triacylglycerol metabolism." Am J Clin Nutr 71:232S-7S (2000).

Rodgers, P. J., "No effect of n-3 long-chain polyunsaturated fatty acid (EPA and DHA) supplementation on depressed mood and cognitive function: a randomised controlled trial" British Journal of Nutrition, 99:421-431, (2008).

Rodriguez, Y., et al., "Long-chain ω6 polyunsaturated fatty acids in erythrocyte phospholipids are associated with insulin resistance in non-obese type 2 diabetics." Clinica Chimica Acta 354:195-199 (2005).

Rubins, H.B., et al., (1995). Distribution of lipids in 8,500 men with coronary artery disease: Department of Veterans Affairs HDL Intervention Trial Study Group. Am. J. Cardiol. 75: 1196-1201.

Rubins, H.B., et al., (1999). Gemfibrozil for the prevention of coronary heart disease in men with low levels of high-density lipoprotein cholesterol. Veterans Affairs HDL-C intervention trial study group. N. Eng. J. Med. 341: 410-418.

Ruiz-Narvaez, E.A., et al., "Abdominal obesity and hyperglycemia mask the effect of a common APOC3 haplotype on the risk of myocardial infarction." Am J Clin Nutr 87:1932-8 (2008).

Rustan, A.C., et al., "Eicosapentaenoic acid reduces hepatic synthesis and secretion of triacylglycerol by decreasing the activity of acyl-coenzyme A:1,2-diacylglycerol acyltransferase." J. Lipid Res. 29:1417-1426 (1988).

Rustan, A.C., et al., "Postprandial decrease in plasma unesterified fatty acids during n-3 fatty acid feeding is not caused by accumulation of fatty acids in adipose tissue." Biochimica et Biophysica Acta 1390.245-25 (1998).

Rustan, A.C., et al., "Eicosapentaenoic acid inhibits cholesterol esterification in cultured parenchymal cells and isolated microsomes from rat liver." J. Bio. Chem. 263(17):8126-32 (1988).

Ryan, A.M., et al., "Enteral nutrition enriched with eicosapentaenoic acid (EPA) preserves lean body mass following esophageal cancer surgery: results of a double-blinded randomized controlled trial." Ann Surg 249:355-363 (2009).

Saito, J., et al., "Mechanisms of enhanced production of PGI2 in cultured rat vascular smooth muscle cells enriched with eicosapentaenoic acid." Atherosclerosis 131: 219-228 (1997).

Saito et al., Effects of EPA on coronary artery disease in hypercholesterolemic patients with multiple risk factors: Sub-analysis of primary prevention cases from the Japan EPA Lipid Intervention Study (JELIS), (Atherosclerosis (2008) 200:135-140).

Samuels, A., et al., Office Practice of Neurology, Chapter 122, Huntington's Disease, pp. 654-655, 1996.

Sanders, T.A., et al., "Triglyceride-lowering effect of marine polyunsaturates in patients with hypertriglyceridemia." Arterioscler. Thromb. Vasc. Biol. 5:459-465 (1985).

Sanders, T.A., et al., "Influence of n-3 fatty acids on blood lipids in normal subjects" Journal of Internal Medicine. 225:99-104,1989.

Sanders, et al., "Influence of an algal triacylglycerol containing docosahexaenoic acid (22:6n-3) and docosapentaenoic acid (22:5n-6) on cardiovascular risk factors in healthy men and women," British Journal of Nutrition (2006), 95, 525-531.

Sanders, T.A., et al., "Effect of varying the ratio of n-6 to n-3 fatty acids by increasing the dietary intake of α-linolenic acid, eicosapentaenoic and docosahexaenoic acid, or both on fibrinogen and clotting factors VII and XII in persons aged 45-70 y: the OPTILIP Study." Am J Clin Nutr 84:513-22 (2006).

Sasaki, Y.F., et al., "Bio-anticlastogenic effects of unsaturated fatty acids included in fish oil -docosahexaenoic acid, docosapentaenoic acid, and eicosapentaenoic acid—in cultured Chinese hamster cells." Mutation Research, 320: 9-22 (1994).

Sato, M., et al., "General Pharmacological Studies on 5 8 11 14 17 Eicosapentaenoic Acid Ethyl Ester EPA-E", Folia Pharmacol JPN, (1989) 94 (1), 35-48.

Satoh, N., et al., "Purified eicosapentaenoic acid reduces small dense LDL, remnant lipoprotein particles, and C-reactive protein in metabolic syndrome." Diabetes Care, 30(1): 144-146 (2007).

Schectman, G., et al., "Heterogeneity of Low Density Lipoprotein Responses to Fish-Oil Supplementation in Hypertriglyceridemic Subjects." Arteriosler. Thromb. Vasc. Biol. 9:345-354 (1989).

Schectman, G & Hiatt, J., (1996). Drug therapy for hypercholesterolemia in patients with cardiovascular disease: factors limiting achievement of lipid goals. Am. J. Med. 100: 197-204.

Schmidt, E.B., et al., "Lipoprotein-associated phospholipase A2 concentrations in plasma are associated with the extent of coronary artery disease and correlate to adipose tissue levels of marine n-3 fatty acids." Atherosclerosis 196: 420-424 (2008).

Schmitz, G., et al., "The opposing effects of n-3 and n-6 fatty acids." Progress in Lipid Research, 47:147-155 (2008).

Schwarz, S., et al., "Lycopene inhibits disease progression in patients with benign prostate hyperplasia." J. Nutr. 138: 49-53 (2008).

Serhan, C.N., et al., "Resolvins: A family of bioactive products of omega-3 fatty acid transformation circuits initiated by aspirin treatment that counter proinflammation signals." J. Exp. Med. 196:1025-1037 (2002).

Shah, S., et al., "Eicosapentaenoic Acid (EPA) as an Adjunct in the Treatment of Schizophrenia", Schizophrenia Research, vol. 29, No. 1/02, Jan. 1998.

Shan, Z., et al., "A combination study of spin-trapping, LC/ESR and LC/MS on carbon-centred radicals formed from lipoxygenase-catalysed peroxidation of eicosapentaenoic acid." Free Radical Research, 43(1):13-27 (2009).

Shimizu, H., et al., "Long-term effect of eicosapentaenoic acid ethyl (EPA-E) on albuminuria of non-insulin dependent diabetic patients." Diabetes Research and Clinical Practice 28: 35-40 (1995).

Shinozaki K. et al., "The long-term effect of Eicosapentaenoic acid on serum levels of lipoprotein (a) and lipids in patients with vasciular disease" J Atheroscler Thromb. 2(2):207-9 (1996).

Sierra, S., et al., "Dietary eicosapentaenoic acid and docosahexaenoic acid equally incorporate as decosahexaenoic acid but differ in inflammatory effects." Nutrition 24: 245-254 (2008).

Silvers, K. M., et al., "Randomised double-blind placebo-controlled trial of fish oil in the treatment of depression," Prostagandins, Leukotrienes and Essential Fatty Acids. 72:211-218 (2005).

Simoens, C.M., et al., "Inclusion of 10% fish oil in mixed medium-chain triacylglycerol-longchain triacylglycerol emulsions increases plasma triacylglycerol clearance and induces rapid eicosapentaenoic acid (20:5n-3) incorporation into blood cell phospholipids." Am J Clin Nutr 88: 282-8 (2008).

Simon, J.A., et al., "Serum Fatty Acids and the Risk of Coronary Heart Disease", American Journal of Epidemiology, 142(5):469-476, 1995.

Singh, R.B., et al., "Randomized, double-blind, placebo-controlled trial of fish oil and mustard oil in patients with suspected acute myocardial infarction: the Indian experiment of infarct survival—4." Cardiovascular Drugs and Therapy 11:485-491 (1997).

Sirtori, C.R., et al., "One-year treatment with ethyl esters of n-3 fatty acids in patients with hypertriglyceridemia and glucose intolerance—Reduced triglyceridemia, total cholesterol and increased HDL-C." Atherosclerosis 137: 419-427 (1998).

Skinner JS, Cooper A, & Feder GS and on behalf of the Guideline Development Group. "Secondary prevention for patients following a myocardial infarction; summary of NICE guidance," Heart 2007; 93:862-864.

Smith et al., Pharmacokinetics and Pharmacodynamics of Epoetin Delta in Two Studies in Health Volunteers and Two Studies in Patients with Chronic Kidney Disease, Clinical Therapeutics/vol. 29, No. 7, 2007, pp. 1368-1380.

Sohma, R., et al., "Protective effect of n-3 polyunsaturated fatty acid on primary culture of rat hepatocytes without glycemic alterations." Journal of Gastroenterology and Hepatology 22: 1965-1970 (2007).

Spector, A.A., et al., "Epoxyeicosatrienoic acids (EETs): metabolism and biochemical function." Progress in Lipid Research 43: 55-90 (2004).

Spector, A.A., "Arachidonic acid cytochrome P450 epoxygenase pathway." Journal of Lipid Research, 50: S52-S56 (2009) (published online on Oct. 23, 2008.).

Springer, T.A., "Traffic signals for lymphocyte recirculation and leukocyte emigration: The multistep paradigm." Cell, 76: 301-314 (1994).

Squires et al., Low-Dose, Time-Release Nicotinic Acid: Effects in Selected Patients With Low Concentrations of High-Density Lipoprotein Cholesterol, May Clin Proc 67:855-860, 1992.

Srinivas, et al., "Controlled release of lysozyme from succinylated gelatin microspheres," J. Biomater. Sci., Polymer Ed., vol. 12(2):137-148 (2001).

Stalenhoef, A.F.H., et al., "The effect of concentrated n-3 fatty acids versus gemfibrozil on plasma lipoproteins, low density lipoprotein heterogeneity and oxidizability in patients with hypertrygliceridemia." Atherosclerosis 153: 129-138 (2000).

Stark, K.D., et al., "Effect of a fish-oil concentrate on serum lipids in postmenopausal women receiving and not receiving hormone replacement therapy in a placebo-controlled, double-blind trial." Am J Clin Nutr 72:389-94 (2000).

Stark, K.D. & Holub, B.J., Differential eicosapentaenoic acid elevations and altered cardiovascular disease risk factor responses after supplementation with docosahexaenoic acid in postmenopausal women receiving and not receiving hormone replacement therapy, Am. J. Clin. Nutr., vol. 79, pp. 765-773 (2004).

Stark, K.D., "The percentage of n-3 highly unsaturated fatty acids in total HUFA as a biomarker for omega-3 fatty acid status in tissues." Lipids 43:45-53 (2008).

Stoll, A.L., et al., Arch. Gen. Psychiatry, vol. 56, "Omega 3 Fatty Acids in Bipolar Disorder", pp. 407-412, May 1999.

Su, K. P., et al. "Omega-3 Fatty Acids in Major Depressive Disorder A Preliminary Double-Blind, Placebo-Controlled Trial" European Neuropsychopharmacology, 13:267-271 (2003).

Sugiyama, E., et al., "Eicosapentaenoic acid lowers plasma and liver cholesterol levels in the presence of peroxisome proliferators-activated receptor alpha." Life Sciences, 83:1928 (2008).

Superko et al., "Lipid Management to Reduce Cardiovascular Risk: A New Strategy is Required," Circulation 2008, 117:560-568.

Surette, M.E., et al., "Evidence for mechanisms of the hypotriglyceridemic effect of n-3 polyunsaturated fatty, acids." Biochimica et Biophysic Acta, 1126: 199-205 (1992).

Tamura, et al., "Study of the Clinical Usefulness of Ethyl Icosapentate (MND-21) in Long-Term Treatment of Hyperlipaemic Patients." J Clin Thera & Medicines 1991; 7:1817-1834.

Tanaka, K.T., et al., "Reduction in the recurrence of stroke by eicosapentaenoic acid for hypercholesterolemic patients—Subanalysis of the JELIS trial." Stroke, 39(7):2052-8 (2008).

Tatarczyk, et al., "Analysis of long-chain ω-3 fatty acid content in fish-oil supplements," Wien Kim Wochenschr (2007) 119/13-14: 417-422.

Taylor et al., Arterial Biology for the Investigation of the Treatment Effects of Reducing Cholesterol (ARBITER) 2: A Double-Blind, Placebo-Controlled Study of Extended-Release Niacin on Atherosclerosis Progression in Secondary Prevention Patients Treated With Statins, Circulation 2004;110;3512-3517.

Tedgui, A., et al., "Anti-inflammatory mechanisms in the vascular wall." Circ. Res. 88:877-887 (2001).

Terano, et al., "Effect of Oral Administration of Highly Purified Eicosapentaenoic Acid on Platelet Function, Blood Vicosity and Red Cell Deformability in Healthy Human Subjects," Atherosclerosis, 46 (1983) 321-331.

Theilla, M., et al., "A diet enriched in eicosapentanoic acid, gamma-linolenic acid and antioxidants in the prevention of new pressure ulcer formation in critically ill patients with acute lung injury: A randomized, prospective, controlled study." Clinical Nutrition 26: 752-757 (2007).

Thies, F., et al., "Dietary supplementation with eicosapentaenoic acid, but not with other long-chain n-3 or n-6 polyunsaturated fatty acids, decreases natural killer cell activity in healthy subjects aged >55 y." Am J Clin Nutr 73:539-48 (2001).

Thies, F., et al., "Association of n-3 polyunsaturated fatty acids with stability of atherosclerotic plaques: a randomised controlled trial." Lancet 361: 477-85 (2003).

Tirosh et al., Changes in Triglyceride Levels and Risk for Coronary Heart Disease in Young Men,: 2007 American College of Physicians, pp. 377-385.

Torrejon, C. et al., "n-3 Fatty acids and cardiovascular disease: Actions and molecular mechanisms," Prostaglandins Leukotrienes & Essent. Fatty Acids (2007), doi:10.1016/j.plefa.2007.10.014.

Tsuruta K., et al.,"Effects of purified eicosapentaenoate ethyl ester on fibriolytic capacity in patients with stable coronary artery disease and lower extremity ischaemia" Coron Artery Dis. 7(11):837-42 (Nov. 1996).

Ullian, M.E., "Fatty acid inhibition of angiotensin II-stimulated inositol phosphates in smooth muscle cells." Am J Physiol Heart Circ Physiol (Nov. 1996).

Urakaze, M., et al., "Infusion of emulsified trieicosapentaenoylglycerol into rabbits. The effects on platelet aggregation, polymorphonuclear leukocyte adhesion, and fatty acid composition in plasma and platelet phosphollpids", Thromb. Res. (1986) 44(5), pp. 673-682.

US Food and Drug Administration and Dept of Health and Human Services. Substances affirmed as generally recognized as safe: Menhaden Oil. Fed Register 1997; 62:30751-30757.

Vaddadi, K. S., et al., "A Randomised, Placebo-Controlled, Double-Blind Study of Treatment of Huntington's Disease with Unsaturated Fatty Acids" Clinical Neuroscience and Neuropathology, 13(1):29-33 (Jan. 2002).

Van der Steeg, W.A., et al., "High-density lipoprotein cholesterol, high-density lipoprotein particle size, and apolipoprotein A-I: Significance for cardiovascular risk—the IDEAL and EPIC-Norfolk studies." J. Am. Coll. Cardiol. 51;634-642 (2008).

Vasudevan et al., "Effective Use of Combination of Lipid Therapy", Curr. Atheroscl. Rep., vol. 8, pp. 76-84 (2006).

Vedin, I., et al., "Effects of docosahexaenoic acid-rich n-3 fatty acid supplementation on cytokine release from blood mononuclear leukocytes: the OmegAD study." Am J Clin Nutr 87:1616-22 (2008).

Vidgren, H.M., et al., "Incorporation of n-3 fatty acids into plasma lipid fractions, and erythrocyte membranes and platelets during dietary supplementation with fish, fish oil, and docosahexaenoic acid-rich oil among healthy young men." Lipids 32: 697-705 (1997).

Volcik, K.A., et al., "Peroxisome proliferator-activated receptor αgenetic variation interacts with n-6 and long-chain n-3 fatty acid intake to affect total cholesterol and LDL-cholesterol concentrations in the Atherosclerosis Risk in Communities Study." Am J Clin Nutr 87:1926-31 (2008).

Von Schacky, C., et al., "The Effect of Dietary w-3 Fatty Acids on Cornoray Atherosclerosis: A Randomized, Double-Blind, Placebo-Controlled Trial", American College of Physicians—American Society of Internal Medicine, 130(7):554-562, 1999.

Von Schacky, C., "A review of omega-3 ethyl esters for cardiovascular prevention and treatment of increased blood triglyceride levels." Vascular Health and Risk Management 2(3): 251-262 (2006).

Wada, M., et al., "Enzymes and receptors of prostaglandin pathways with arachidonic acid-derived versus eicosapentaenoic acid-derived substrates and products." J. Biol. Chem. 282(31): 22254-22266 (2007).

Walldius, G., et al., "Editorial: Rationale for using apolipoprotein B and apolipoprotein A-I as indicators of cardiac risk and as targets for lipid-lowering therapy." European Heart Journal 26, 210-212 (2005).

Wander, R.C., et al., "Influence of long.chain polyunsaturated fatty acids on oxidation of low density lipoprotein." Prostaglandins, Leukotrienes and Essential Fatty Acids 59(2):143-151 (1998).

Wang, C., et al., "n-3 Fatty acids from fish or fish-oil supplements, but not α-linolenic acid, benefit cardiovascular disease outcomes in primary- and secondary-prevention studies: a systematic review." Am J Clin Nutr 84:5-17 (2006).

Wang, L., et al., "Triglyceride-rich lipoprotein lipolysis releases neutral and oxidized FFAs that induce endothelial cell inflammation." J. Lipid Res. 50:204-213 (2009).

Warren, S.T., Science, vol. 271, "The Expanding World of Trinucleotide Repeats", pp. 1374-1375, Mar. 8, 1996.

Watanabe, I., et al., "Usefulness of EPA-E (eicosapentaenoic acid ethyl ester) in preventing neointimal formation after vascular injury", Kokyu to Junkan (1994), 42(7), pp. 673-677.

Weaver, K.L., et al., "Effect of Dietary Fatty Acids on Inflammatory Gene Expression in Healthy Humans." J. Biol. Chem., 284(23): 15400-15407 (2009) (published online Apr. 9, 2009.).

Weber, P., "Triglyceride-lowering effect of n-3 long chain polyunsaturated fatty acid: eicosapentaenoic acid vs. docosahexaenoic acid." Lipids 34: S269 (1999).

Westerveld H.T. et al., "Effects of low-dose EPA-Eon glycemic control, lipid profile, lipoprotein(a), platelet aggretation, viscosity, and platelet and vessel wall interaction in NIDDM" Diabetes Care 16(5):683-8 (May 1993).

Westphal, S., et al., "Postprandial chylomicrons and VLDLs in severe hypertriacylglycerolemia are lowered more effectively than are chylomicron remnants after treatment with n23 fatty acids." Am J Clin Nutr 71:914-20 (2000).

Whelan, J., et al., "Evidence that dietary arachidonic acid increases circulating triglycerides." Lipids 30, 425-429 (1995).

Wierzbicki, A.S., "Editorial: Newer, lower, better? Lipid drugs and cardiovascular disease—the continuing story." Int J Clin Pract, 61(7):1064-1067 (2007).

Wierzbicki, A.S., "Editorial: Raising HDL-C: back to the future?" Int J Clin Pract, 61(7): 1069-1071 (2007).

Willumsen, N., et al., "Eicosapentaenoic acid, but not docosahexaenoic acid, increased, mitochondrial fatty acid oxidation and upregulates 2,3-dienoyl-CoA reductase gene expression in rats." Lipids, 31:579-592 (1996).

Willumsen, N. et al., Biochimica et Biophysica Acta. vol. 1369, "On the effect of 2-deuterium- . . . ", pp. 193-203, 1998.

Wilson Omega 3 fish oil: EPA versus DHA (Dietivity.com, 2006, 1-16).

Wilt, V.M. & Gumm, J.G. (1997). "Isolated" low high-density lipoprotein cholesterol. Ann. Pharmacol. 31: 89-97.

Wink et al., Effect of very-low-dose niacin on high-density lipoprotein in patients undergoing long-term statin therapy, Am Heart J 2002;143:514-8.

Wojenski, C.M., et al., "Eicosapentaenoic acid ethyl ester as an antithrombotic agent: comparison to an extract of fish oil." Biochimica et Biophysica Acta. 1081:33-38 (1991).

Wong, S.H., et al., "Effects of eicosapentaenoic and docosahexaenoic acids on Apoprotein B mRNA and secretion of very low density lipoprotein in HepG2 cells." Arterioscler. Thromb. Vasc. Biol. 9;836-841 (1989).

Woodman, R. J., et al., "Effects of Purified Eicoaspentaenoic and Docosahexaenoic Acids on Glycemic Control, Blood Pressure, and Serum Lipids in Type 2 Diabetic Patients with Treated Hypertension" The American Journal of Clinical Nutrition: Official Journal of the American Society for Clinical Nutrition, Inc. 76(5):1007-1015 (Nov. 1, 2002).

Woodman, R.J., et al., "Effects of purified eicosapentaenoic acid and docosahexaenoic acid on platelet, fibrinolytic and vascular function in hypertensive type 2 diabetic patients." Atherosclerosis 166: 85-93 (2003).

Xiao, Y.-F., et al., "Blocking effects of polyunsaturated fatty acids on $Na^+$ channels of neonatal rat ventricular myocytes." Proc. Natl. Acad. Sci. 92: 11000-11004 (1995).

Xiao, Y.-F., et al., "Fatty acids suppress voltage-gated $Na^+$ currents in HEK293t cells transfected with the a-subunit of the human cardiac $Na^+$channel." Proc. Natl. Acad. Sci. 95: 2680-2685 (1998).

Xiao, Y.F., et al., "Inhibitory effect of n-3 fish oil fatty acids on cardiac $Na^+/Ca^{2+}$ exchange currents in HEK293t cells." Biochemical and Biophysical Research Communications 321: 116-123 (2004).

Xydakis, A M et al., "Combination therapy for combined dyslipidemia," American Journal of Cardiology, 20021120 US, vol. 90, No. 10 Suppl. 2, Nov. 20, 2002, p. 21 K-29K.

Yamamoto, H. et al., Improvement of coronary vasomotion with Eicosapentaenoic acid does not inhibit acetylcholine-induced coronary vasospasm in patients with variant angina: Jpn Cir J. 59(9):608-16 (Sep. 1995).

Yamamoto, K., et al., "4-Hydroxydocosahexaenoic acid, a potent Peroxisome Proliferator-Activated Receptor C agonist alleviates the symptoms of DSS-induced colitis." Biochemical and Biophysical Research Communications 367: 566-572 (2008).

Yamashita, Atsushi, et al., J. Biochem., vol. 122, No. 1, "Acyltransferases and Transaclyases Involved in Fatty Acid Remoding of Phospholipids and Metabolism of Bioactive Lipids in Mammalian Cells", pp. 1-16, 1997.

Yamashita, N., et al., "Inhibition of natural killer cell activity of human lymphocytes by eicosapentaenoic acid." Biochem. Biophys. Res. Comm. 138(3): 1058-1067 (1986).

Yamazaki, et. al., "Dissolution tests by RDC method for soft gelatin capsules containing ethyl icosapentate,", Pharm. Tech. Japan, vol. 15, No. 4, pp. 595-603 (1999). Abstract.

Yamazaki, K., et al., "Changes in fatty acid composition in rat blood and organs after infusion of eicosapentaenoic acid ethyl ester", Biochim. Biophys. Acta (1992), 1128(1), 35-43.

Yang, S.P., et al., "Eicosapentaenoic acid attenuates vascular endothelial growth factor-induced proliferation via inhibiting Flk-1 receptor expression in bovine carotid artery endothelial cells." J. Cell. Physio. 176:342-349 (1998).

Yano T, Mizuguchi K, Takasugi K, Tanaka Y, Sato M. "Effects of ethyl all-cis-5,8,11,14,17-icosapentaenoate on low density lipoprotein in rabbits," Yakugaku Zasshi 1995; 115:843-51.

Yano, T., et al., "Effects of ethyl-all-cis-5,8,11,14,17-icosapentaenoate (EPA-E), pravastatin and their combination on serum lipids and intimal thickening of cuff-sheathed carotid artery in rabbits." Life Sciences, 61(20):2007-2015 (1997).

Yerram, N. R., et al., "Eicosapentaenoic acid metabolism in brain microvessel endothelium: effect on prostaglandin formation." J. Lipid Res.30:1747-1757 (1989).

Yokoyama et al., "Effects of eicosapentaenoic acid on major coronary events in hypercholesterolaemic patients (JELIS): a randomized open-label, blinded endpoint analysis", Lancet, vol. 369, pp. 1090-1098 (2007).

Yoshimura, T., et al., Effects of highly purified eicosapentaenoic acid on plasma beta thromboglobulin level and vascular reactivity to angiotensin II, Artery (1987) 14(5) pp. 295-303.

Zaima, N., et al., "*Trans* geometric isomers of EPA decrease LXRa-induced cellular triacylglycerol via suppression of SREBP-1c and PGC-β." J. Lipid Res. 47: 2712-2717 (2006).

Zanarini, et al., "Omega-3 Fatty Acid Treatment of Women with Borderline Personality Disorder: A Double-Blind, Placebo-Controlled Pilot Study," Am J Psychiatry 2003; 160:167-169.

Zhang, M., et al., "Effects of eicosapentaenoic acid on the early stage of type 2 diabetic nephropathy in KKAy/Ta mice: involvement of anti-inflammation and antioxidative stress." Metabolism Clinical and Experimental 55:1590-1598 (2006).

Zhang, Y.W., et al., "Pretreatment with eicosapentaenoic acid prevented hypoxia/reoxygenation-induced abnormality in endothelial gap junctional intercellular communication through inhibiting the tyrosine kinase activity." Prostaglandins, Leukotrienes and Essential Fatty Acids 61(1): 33-40 (1999).

Zhang, Y.W., et al., "Inhibitory effects of eicosapentaenoic acid (EPA) on the hypoxia/reoxygenation-induced tyrosine kinase activation in cultured human umbilical vein endothelial cells." Prostaglandins, Leukotrienes and Essential FattyAcids 67(4):253-261 (2002).

Zhao, G., et al., "Dietary α-linolenic acid reduces inflammatory and lipid cardiovascular risk factors in hypercholesterolemic men and women." J. Nutr. 134: 2991-2997 (2004).

Zhao, G. et al., "Dietary α-linolenic acid inhibits proinflammatory cytokine production by peripheral blood mononuclear cells in hypercholesterolemic subjects." Am J Clin Nutr 85:385-91 (2007).

Ziegler, D., et al., "Treatment of symptomatic diabetic polyneuropathy with the antioxidant alipoic acid: a 7-month multicenter randomized controlled trial (ALADIN III Study)." Diabetes Care 22:1296-1301 (1999).

Zuijdgeest-van Leeuwen, SD, et al., "Eicosapentaenoic acid inhibits lipolysis in weight-losing cancer patients as well as in healthy volunteers," Eur J Gastroenterol & Hepatol 1998; 10(12):A67.

Zuijdgeest-van Leeuwen, S.D., et al., "Incorporation and washout of orally administered n-3 fatty acid ethyl esters in different plasma lipid fractions." British Journal of Nutrition 82:481-488 (1999).

Zuijdgeest-van Leeuwen, et al., "N-3 Fatty Acids Administered as Triacylglycerols or as Ethyl Esters Have Different Effects on Serum Lipid Concentrations in Healthy Subjects," N-3 Fatty Acids, Lipid Metabolism and Cancer, Feb. 2000, pp. 89-100.

Agren, J.J., et al., "Fish diet, fish oil and docosahexaenoic acid rich oil lower fasting and postprandial plasma lipid levels." Eur J Clin Nutr. 1996;50:765-771.

Baigent, C., et al., "Efficacy and safety of cholesterol-lowering treatment: prospective meta-analysis of data from 90,056 participants in 14 randomised trials of statins." Lancet. 2005;366:1267-1278.

Balk, E.M., et al., "Effects of omega-3 fatty acids on serum markers of cardiovascular disease risk: a systematic review. Atherosclerosis." 2006;189:19-30.

Bays, H.E., et al., "Long-term up to 24-month efficacy and safety of concomitant prescription omega-3-acid ethyl esters and simvastatin in hypertriglyceridemic patients." Curr Med Res Opin. 2010;26:907-915.

Berge, R.K., et al., "In contrast with docosahexaenoic acid, eicosapentaenoic acid and hypolipidaemic derivatives decrease hepatic synthesis and secretion of triacylglycerol by decreased diacylglycerol acyltransferase activity and stimulation of fatty acid oxidation." Biochem J. 1999; 343(Pt 1):191-197.

Campos, H., et al., "Lowdensity lipoprotein size, pravastatin treatment, and coronary events." JAMA. 2001;286:1468-1474.

Center for Drug Evaluation and Research. Application No. 21-853, 21654s016, (Omacor). Statistical Review and Evaluation: Clinical Studies, Omacor (omega-3 acid ethyl ester) Capsules, 4 grams/day; 2007. Available at: http://www.accessdata.fda.gov/drugsatfda_docs/nda/2007/021853s000;%20021654s016_StatR.pdf. Accessed Jan. 26, 2012.

Center for Drug Evaluation and Research. Approval Package for: 21-654 (Omacor/Lovaza). Statistical Review; 2004. Available at: http://www.accessdata.fda.gov/drugsatfda_docs/nda/2004/21-654_Omacor_AdminCorres_P1.pdf. Accessed Jan. 26, 2012.

Chapman, M.J., et al., "Cholesteryl ester transfer protein: at the heart of the action of lipid-modulating therapy with statins, fibrates, niacin, and cholesteryl ester transfer protein inhibitors." Eur Heart J. 2010;31:149-164.

Cohen, J.D., et al., "30-year trends in serum lipids among United States adults: results from the National Health and Nutrition Examination Surveys II, III, and 1999-2006." Am J Cardiol. 2010;106:969-975.

Conquer, J.A., et al., "Effect of supplementation with different doses of DHA on the levels of circulating DHA as non-esterified fatty acid in subjects of Asian Indian background. J Lipid Res." 1998;39:286-292.

Conquer, J.A., et al., "Supplementation with an algae source of docosahexaenoic acid increases (n-3) fatty acid status and alters selected risk factors for heart disease in vegetarian subjects." J Nutr. 1996;126: 3032-3039.

Davidson, M.H., et al., "Effects of docosahexaenoic acid on serum lipoproteins in patients with combined hyperlipidemia: a randomized, doubleblind, placebo-controlled trial." J Am Coll Nutr. 1997;16:236-243.

Egert, S., et al., "Dietary alpha-linolenic acid, EPA, and DHA have differential effects on LDL fatty acid composition but similar effects on serum lipid profiles in normolipidemic humans " J Nutr. 2009;139:861-868.

Epadel® [Complete prescribing information]. Update (Version 5). Tokyo, Japan: Mochida Pharmaceutical; Jan. 2007. (English translation).

Friedewald, W.T., et al., "Estimation of the concentration of low-density lipoprotein cholesterol in plasma, without use of the preparative ultracentrifuge." Clin Chem. 1972;18:499-502.

Gould, A.L., et al., "Cholesterol reduction yields clinical benefit: impact of statin trials." Circulation. 1998;97:946-952.

Haney, E.M., et al., "Screening for lipid disorders in children and adolescents; Systematic evidence review for the U.S. Preventive Services Task Force (evidence synthesis)." No. 47. Rockville, MD: Agency for Healthcare Research and Quality, US Department of Health and Human Services; AHRQ Publication No. 07-0598-EF-1; Jul. 2007. Available at: http://www.uspreventiveservicestaskforce.org/uspstf07/chlipid/chlipidsyn.pdf. Accessed Mar. 23, 2011.

Hannah, J., et al., "Effect of dietary fatty acids on LDL binding." Ann N Y Acad Sci. 1993; 683:178-182.

Hartweg, J., et al., "Potential impact of omega-3 treatment on cardiovascular disease in type 2 diabetes." Curr Opin Lipidol. 2009;20:30-38.

Hirano, R., et al., "Regulation by long-chain fatty acids of the expression of cholesteryl ester transfer protein in HepG2 cells." Lipids. 2001;36:401-406.

Jacobson, T.A., et al., "Effects of eicosapentaenoic acid and docosahexaenoic acid on low-density lipoprotein cholesterol and other lipids: A review." J. Clin. Lipidology, vol. 6, pp. 5-18 (2012).

Kris-Etherton, P.M., et al., "American Heart Association Nutrition Committee. Fish consumption, fish oil, omega-3 fatty acids, and cardiovascular disease." Circulation. 2002;106:2747-2757.

Law, M.R., et al., "Quantifying effect of statins on low density lipoprotein cholesterol, ischaemic heart disease, and stroke: systematic review and meta-analysis." Br Med J. 2003;326:1423-1427.

Lien, E.L., "Toxicology and safety of DHA." Prostaglandins Leukot Essent Fatty Acids. 2009;81:125-132.

Lindsey, S., et al., "Low density lipoprotein from humans supplemented with n-3 fatty acids depresses both LDL receptor activity and LDLr mRNA abundance in HepG2 cells." J Lipid Res. 1992;33:647-658.

Lu, G., et al., "Omega-3 fatty acids alter lipoprotein subfraction distributions and the in vitro conversion of very low density lipoproteins to lowdensity lipoproteins." J Nutr Biochem. 1999;10:151-158.

Maki, K.C., et al., "Baseline lipoprotein lipids and low-density lipoprotein cholesterol response to prescription omega-3 acid ethyl ester added to simvastatin therapy." Am J Cardiol. 2010;105:1409-1412.

Martin-Jadraque, R., et al., "Effectiveness of Low-Dose Crystalline Nicotinic Acid in Men With Low High-Density Lipoprotein Cholesterol Levels." Arch. Intern. Med., vol. 156, pp. 1081-1088 (May 27, 1996).

Mora, S., et al., "LDL particle subclasses, LDL particle size, and carotid atherosclerosis in the Multi-Ethnic Study of Atherosclerosis (MESA)." Atherosclerosis. 2007;192:211-217.

Morton, R.E., "Specificity of lipid transfer protein for molecular species of cholesteryl ester." J Lipid Res. 1986;27:523-529.

Nestel, P.J., "Effects of N-3 fatty acids on lipid metabolism." Ann Rev Nutr. 1990;10:149-167.

Roach, P.D., et al., "The effects of dietary fish oil on hepatic high density and low density lipoprotein receptor activities in the rat." FEBS Lett. 1987;222: 159-162.

Robinson, J.G., et al., "Meta-analysis of the relationship between non-high-density lipoprotein cholesterol reduction and coronary heart risk." J Am Coll Cardiol. 2009;53: 316-322.

Ryan, A.S., et al., "Clinical overview of algal-docosahexaenoic acid: effects on triglyceride levels and other cardiovascular risk factors." Am J Ther. 2009;16:183-192.

Schaefer, E.J., et al., "Effects of eicosapentaenoic acid, docosahexaenoic acid, and olive oil on cardiovascular disease risk factors [abstract 20007]." Circulation. 2010;122:A20007.

Schectman, G., et al., "Dietary fish oil decreases low-density-lipoprotein clearance in nonhuman primates." Am J Clin Nutr. 1996;64:215-221.

Surette, M.E., et al., "Dependence on dietary cholesterol for n-3 polyunsaturated fatty acidinduced changes in plasma cholesterol in the Syrian hamster." J Lipid Res. 1992;33:263-271.

Wu, W.H., et al., "Effects of docosahexaenoic acid supplementation on blood lipids, estrogen metabolism, and in vivo oxidative stress in postmenopausal vegetarian women." Eur J Clin Nutr. 2006;60:386-392.

U.S. Appl. No. 13/198,221.
U.S. Appl. No. 13/284,408.
U.S. Appl. No. 13/349,150.
U.S. Appl. No. 13/349,153.
U.S. Appl. No. 13/349,157.

Bays, H.E., Eicosapentaenoic Acid Ethyl Ester (AMR101) Therapy in Patients With Very High Triglyceride Levels (from the Multi-center, plAcebo-controlled, Randomized, double-blINd, 12-week study with an open-label Extension [MARINE] Trial) Am J Cardiol 2011;108:682-690.

Cefali, E.A, et al., "Aspirin reduces cutaneous flushing after administration of an optimized extended-release niacin forumulation." International Journal of Clinical Pharmacology and Therapeutics, vol. 45—No. 2/2007 (78-88).

Connor et al., "Seminarins in thrombosis and hemostasis" (1988) 14:271-284.

Fisher et al., Journal of Biological Chemistry (2001) 276(3) 27855-27863.

Product brochure: "PLUSEPA® "Super Critically" Different from Other Omega-3 Fish Oil Supplements for Depression and ADHD," by Minami Nutrition (Apr. 2009, pp. 1-6).

Sacks, Frank M., "The apolipoprotein story," Atherosclerosis Supplements 7 (2006) 23-27.

\* cited by examiner

METHODS OF TREATING HYPERTRIGLYCERIDEMIA

This application is a continuation of U.S. Ser. No. 12/702,889, filed Feb. 9, 2010, and claims priority to U.S. provisional application Ser. No. 61/151,291 filed Feb. 10, 2009 and U.S. provisional application Ser. No. 61/173,755 filed Apr. 29, 2009, each of which are incorporated by reference herein in their entireties.

BACKGROUND

Cardiovascular disease is one of the leading causes of death in the United States and most European countries. It is estimated that over 70 million people in the United States alone suffer from a cardiovascular disease or disorder including but not limited to high blood pressure, coronary heart disease, dislipidemia, congestive heart failure and stroke. A need exists for improved treatments for cardiovascular diseases and disorders.

SUMMARY

In various embodiments, the present invention provides methods of treating and/or preventing cardiovascular-related diseases and, in particular, a method of blood lipid therapy comprising administering to a subject in need thereof a pharmaceutical composition comprising eicosapentaenoic acid or a derivative thereof. In one embodiment, the composition contains not more than 10%, by weight, docosahexaenoic acid or derivative thereof, substantially no docosahexaenoic acid or derivative thereof, or no docosahexaenoic acid or derivative thereof. In another embodiment, eicosapentaenoic acid ethyl ester comprises at least 96%, by weight, of all fatty acids present in the composition; the composition contains not more than 4%, by weight, of total fatty acids other than eicosapentaenoic acid ethyl ester; and/or the composition contains about 0.1% to about 0.6% of at least one fatty acid other than eicosapentaenoic acid ethyl ester and docosahexaenoic acid (or derivative thereof).

In one embodiment, a pharmaceutical composition useful in accordance with the invention comprises, consists of or consists essentially of at least 95% by weight ethyl eicosapentaenoate (EPA-E), about 0.2% to about 0.5% by weight ethyl octadecatetraenoate (ODTA-E), about 0.05% to about 0.25% by weight ethyl nonaecapentaenoate (NDPA-E), about 0.2% to about 0.45% by weight ethyl arachidonate (AA-E), about 0.3% to about 0.5% by weight ethyl eicosatetraenoate (ETA-E), and about 0.05% to about 0.32% ethyl heneicosapentaenoate (HPA-E). In another embodiment, the composition is present in a capsule shell. In another embodiment, the composition contains substantially no or no amount of docosahexaenoic acid (DHA) or derivative thereof such as ethyl-DHA (DHA-E).

In another embodiment, the invention provides a method of treating moderate to severe hypertriglyceridemia comprising administering a composition as described herein to a subject in need thereof one to about four times per day.

These and other embodiments of the present invention will be disclosed in further detail herein below.

DETAILED DESCRIPTION

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." Also, the disclosure of ranges is intended as a continuous range including every value between the minimum and maximum values recited as well as any ranges that can be formed by such values. Also disclosed herein are any and all ratios (and ranges of any such ratios) that can be formed by dividing a disclosed numeric value into any other disclosed numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present invention.

In one embodiment, the invention provides a method for treatment and/or prevention of a cardiovascular-related disease. The term "cardiovascular-related disease" herein refers to any disease or disorder of the heart or blood vessels (i.e. arteries and veins) or any symptom thereof. Non-limiting examples of cardiovascular-related disease and disorders include hypertriglyceridemia, hypercholesterolemia, mixed dyslipidemia, coronary heart disease, vascular disease, stroke, atherosclerosis, arrhythmia, hypertension, myocardial infarction, and other cardiovascular events.

The term "treatment" in relation a given disease or disorder, includes, but is not limited to, inhibiting the disease or disorder, for example, arresting the development of the disease or disorder; relieving the disease or disorder, for example, causing regression of the disease or disorder; or relieving a condition caused by or resulting from the disease or disorder, for example, relieving, preventing or treating symptoms of the disease or disorder. The term "prevention" in relation to a given disease or disorder means: preventing the onset of disease development if none had occurred, preventing the disease or disorder from occurring in a subject that may be predisposed to the disorder or disease but has not yet been diagnosed as having the disorder or disease, and/or preventing further disease/disorder development if already present.

In one embodiment, the present invention provides a method of blood lipid therapy comprising administering to a subject or subject group in need thereof a pharmaceutical composition as described herein. In another embodiment, the subject or subject group has hypertriglyceridemia, hypercholesterolemia, mixed dyslipidemia and/or very high triglycerides.

In another embodiment, the subject or subject group being treated has a baseline triglyceride level (or median baseline triglyceride level in the case of a subject group), fed or fasting, of at least about 300 mg/dl, at least about 400 mg/dl, at least about 500 mg/dl, at least about 600 mg/dl, at least about 700 mg/dl, at least about 800 mg/dl, at least about 900 mg/dl, at least about 1000 mg/dl, at least about 1100 mg/dl, at least about 1200 mg/dl, at least about 1300 mg/dl, at least about 1400 mg/dl, or at least about 1500 mg/dl, for example about 400 mg/dl to about 2500 mg/dl, about 450 mg/dl to about 2000 mg/dl or about 500 mg/dl to about 1500 mg/dl.

In one embodiment, the subject or subject group being treated in accordance with methods of the invention has previously been treated with Lovaza® and has experienced an increase in, or no decrease in, LDL-C levels and/or non-HDL-C levels. In one such embodiment, Lovaza® therapy is discontinued and replaced by a method of the present invention.

In another embodiment, the subject or subject group being treated in accordance with methods of the invention exhibits a fasting baseline absolute plasma level of free EPA (or mean thereof in the case of a subject group) not greater than about 0.70 nmol/ml, not greater than about 0.65 nmol/ml, not greater than about 0.60 nmol/ml, not greater than about 0.55 nmol/ml, not greater than about 0.50 nmol/ml, not greater than about 0.45 nmol/ml, or not greater than about 0.40 nmol/ml. In another embodiment, the subject or subject group being treated in accordance with methods of the invention exhibits a baseline fasting plasma level (or mean thereof) of free EPA, expressed as a percentage of total free fatty acid, of not more than about 3%, not more than about 2.5%, not more than about 2%, not more than about 1.5%, not more than about 1%, not more than about 0.75%, not more than about 0.5%, not more than about 0.25%, not more than about 0.2% or not more than about 0.15%. In one such embodiment, free plasma EPA and/or total fatty acid levels are determined prior to initiating therapy.

In another embodiment, the subject or subject group being treated in accordance with methods of the invention exhibits a fasting baseline absolute plasma level of total fatty acid (or mean thereof) not greater than about 250 nmol/ml, not greater than about 200 nmol/ml, not greater than about 150 nmol/ml, not greater than about 100 nmol/ml, or not greater than about 50 nmol/ml.

In another embodiment, the subject or subject group being treated in accordance with methods of the invention exhibits a fasting baseline plasma, serum or red blood cell membrane EPA level not greater than about 70 µg/ml, not greater than about 60 µg/ml, not greater than about 50 µg/ml, not greater than about 40 µg/ml, not greater than about 30 µg/ml, or not greater than about 25 µg/ml.

In another embodiment, methods of the present invention comprise a step of measuring the subject's (or subject group's mean) baseline lipid profile prior to initiating therapy. In another embodiment, methods of the invention comprise the step of identifying a subject or subject group having one or more of the following: baseline non-HDL-C value of about 200 mg/dl to about 400 mg/dl, for example at least about 210 mg/dl, at least about 220 mg/dl, at least about 230 mg/dl, at least about 240 mg/dl, at least about 250 mg/dl, at least about 260 mg/dl, at least about 270 mg/dl, at least about 280 mg/dl, at least about 290 mg/dl, or at least about 300 mg/dl; baseline total cholesterol value of about 250 mg/dl to about 400 mg/dl, for example at least about 260 mg/dl, at least about 270 mg/dl, at least about 280 mg/dl or at least about 290 mg/dl; baseline vLDL-C value of about 140 mg/dl to about 200 mg/dl, for example at least about 150 mg/dl, at least about 160 mg/dl, at least about 170 mg/dl, at least about 180 mg/dl or at least about 190 mg/dl; baseline HDL-C value of about 10 to about 60 mg/dl, for example not more than about 40 mg/dl, not more than about 35 mg/dl, not more than about 30 mg/dl, not more than about 25 mg/dl, not more than about 20 mg/dl, or not more than about 15 mg/dl; and/or baseline LDL-C value of about 50 to about 300 mg/dl, for example not less than about 100 mg/dl, not less than about 90 mg/dl, not less than about 80 mg/dl, not less than about 70 mg/dl, not less than about 60 mg/dl or not less than about 50 mg/dl.

In a related embodiment, upon treatment in accordance with the present invention, for example over a period of about 1 to about 200 weeks, about 1 to about 100 weeks, about 1 to about 80 weeks, about 1 to about 50 weeks, about 1 to about 40 weeks, about 1 to about 20 weeks, about 1to about 15 weeks, about 1 to about 12 weeks, about 1 to about 10 weeks, about 1to about 5 weeks, about 1 to about 2 weeks or about 1 week, the subject or subject group exhibits one or more of the following outcomes:

(a) reduced triglyceride levels compared to baseline;
(b) reduced Apo B levels compared to baseline;
(c) increased HDL-C levels compared to baseline;
(d) no increase in LDL-C levels compared to baseline;
(e) a reduction in LDL-C levels compared to baseline;
(f) a reduction in non-HDL-C levels compared to baseline;
(g) a reduction in vLDL levels compared to baseline;
(h) an increase in apo A-I levels compared to baseline;
(i) an increase in apo A-I/apo B ratio compared to baseline;
(j) a reduction in lipoprotein A levels compared to baseline;
(k) a reduction in LDL particle number compared to baseline;
(l) an increase in LDL size compared to baseline;
(m) a reduction in remnant-like particle cholesterol compared to baseline;
(n) a reduction in oxidized LDL compared to baseline;
(o) no change or a reduction in fasting plasma glucose (FPG) compared to baseline;
(p) a reduction in hemoglobin $A_{1c}$ ($HbA_{1c}$) compared to baseline;
(q) a reduction in homeostasis model insulin resistance compared to baseline;
(r) a reduction in lipoprotein associated phospholipase A2 compared to baseline;
(s) a reduction in intracellular adhesion molecule-1 compared to baseline;
(t) a reduction in interleukin-6 compared to baseline;
(u) a reduction in plasminogen activator inhibitor-1 compared to baseline;
(v) a reduction in high sensitivity C-reactive protein (hsCRP) compared to baseline;
(w) an increase in serum or plasma EPA compared to baseline;
(x) an increase in red blood cell (RBC) membrane EPA compared to baseline; and/or
(y) a reduction or increase in one or more of serum phospholipid and/or red blood cell content of docosahexaenoic acid (DHA), docosapentaenoic acid (DPA), arachidonic acid (AA), palmitic acid (PA), staeridonic acid (SA) or oleic acid (OA) compared to baseline.

In one embodiment, upon administering a composition of the invention to a subject, the subject exhibits a decrease in triglyceride levels, an increase in the concentrations of EPA and DPA (n-3) in red blood cells, and an increase of the ratio of EPA:arachidonic acid in red blood cells. In a related embodiment the subject exhibits substantially no or no increase in RBC DHA.

In one embodiment, methods of the present invention comprise measuring baseline levels of one or more markers set forth in (a)-(y) above prior to dosing the subject or subject group. In another embodiment, the methods comprise administering a composition as disclosed herein to the subject after baseline levels of one or more markers set forth in (a)-(y) are determined, and subsequently taking an additional measurement of said one or more markers.

In another embodiment, upon treatment with a composition of the present invention, for example over a period of about 1 to about 200 weeks, about 1 to about 100 weeks, about 1 to about 80 weeks, about 1 to about 50 weeks, about 1 to about 40 weeks, about 1 to about 20 weeks, about 1 to about 15 weeks, about 1 to about 12 weeks, about 1 to about 10 weeks, about 1 to about 5 weeks, about 1 to about 2 weeks or about 1 week, the subject or subject group exhibits any 2 or more of, any 3 or more of, any 4 or more of, any 5 or more of, any 6 or more of, any 7 or more of, any 8 or more of, any 9 or more of, any 10 or more of, any 11 or more of, any 12 or more of, any 13 or more of, any 14 or more of, any 15 or more of, any 16 or more of, any 17 or more of, any 18 or more of, any 19 or more of, any 20 or more of, any 21 or more of, any 22 or more of, any 23 or more, any 24 or more, or all 25 of outcomes (a)-(y) described immediately above.

In another embodiment, upon treatment with a composition of the present invention, the subject or subject group exhibits one or more of the following outcomes:

(a) a reduction in triglyceride level of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) as compared to baseline;

(b) a less than 30% increase, less than 20% increase, less than 10% increase, less than 5% increase or no increase in non-HDL-C levels or a reduction in non-HDL-C levels of at least about 1%, at least about 3%, at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) as compared to baseline;

(c) substantially no change in HDL-C levels, no change in HDL-C levels, or an increase in HDL-C levels of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) as compared to baseline;

(d) a less than 60% increase, a less than 50% increase, a less than 40% increase, a less than 30% increase, less than 20% increase, less than 10% increase, less than 5% increase or no increase in LDL-C levels or a reduction in LDL-C levels of at least about 5%, at least about 10%, at least about 15%, at least about 20%, at least about 25%, at least about 30%, at least about 35%, at least about 40%, at least about 45%, at least about 50%, at least about 55%, at least about 55% or at least about 75% (actual % change or median % change) as compared to baseline;

(e) a decrease in Apo B levels of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) as compared to baseline;

(f) a reduction in vLDL levels of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(g) an increase in apo A-I levels of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(h) an increase in apo A-I/apo B ratio of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(i) a reduction in lipoprotein (a) levels of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(j) a reduction in mean LDL particle number of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(k) an increase in mean LDL particle size of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(l) a reduction in remnant-like particle cholesterol of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(m) a reduction in oxidized LDL of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(n) substantially no change, no significant change, or a reduction (e.g. in the case of a diabetic subject) in fasting plasma glucose (FPG) of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(o) substantially no change, no significant change or a reduction in hemoglobin $A_{1c}$ ($HbA_{1c}$) of at least about 5%, at least about 10%, at least about 15%, at least about 20%, at least about 25%, at least about 30%, at least about 35%, at least about 40%, at least about 45%, or at least about 50% (actual % change or median % change) compared to baseline;

(p) a reduction in homeostasis model index insulin resistance of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(q) a reduction in lipoprotein associated phospholipase A2 of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(r) a reduction in intracellular adhesion molecule-1 of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(s) a reduction in interleukin-6 of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(t) a reduction in plasminogen activator inhibitor-1 of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(u) a reduction in high sensitivity C-reactive protein (hsCRP) of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(v) an increase in serum, plasma and/or RBC EPA of at least about 5%, at least about 10%, at least about 15%, at least about 20%, at least about 25%, at least about 30%, at least about 35%, at least about 40%, at least about 45%, at least about 50%, at least about 100%, at least about 200% or at least about 400% (actual % change or median % change) compared to baseline;

(w) an increase in serum phospholipid and/or red blood cell membrane EPA of at least about 5%, at least about 10%, at least about 15%, at least about 20%, at least about 25%, at least about 30%, at least about 35%, at least about 40%, at least about 45%, r at least about 50%, at least about 100%, at least about 200%, or at least about 400% (actual % change or median % change) compared to baseline;

(x) a reduction or increase in one or more of serum phospholipid and/or red blood cell DHA, DPA, AA, PA and/or OA of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) compared to baseline; and/or (y) a reduction in total cholesterol of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) compared to baseline.

In one embodiment, methods of the present invention comprise measuring baseline levels of one or more markers set forth in (a)-(y) prior to dosing the subject or subject group. In another embodiment, the methods comprise administering a composition as disclosed herein to the subject after baseline levels of one or more markers set forth in (a)-(y) are determined, and subsequently taking a second measurement of the one or more markers as measured at baseline for comparison thereto.

In another embodiment, upon treatment with a composition of the present invention, for example over a period of about 1 to about 200 weeks, about 1 to about 100 weeks, about 1 to about 80 weeks, about 1 to about 50 weeks, about 1 to about 40 weeks, about 1 to about 20 weeks, about 1 to about 15 weeks, about 1 to about 12 weeks, about 1 to about 10 weeks, about 1 to about 5 weeks, about 1 to about 2 weeks or about 1 week, the subject or subject group exhibits any 2 or more of, any 3 or more of, any 4 or more of, any 5 or more of, any 6 or more of, any 7 or more of, any 8 or more of, any 9 or more of, any 10 or more of, any 11 or more of, any 12 or more of, any 13 or more of, any 14 or more of, any 15 or more of, any 16 or more of, any 17 or more of, any 18 or more of, any 19 or more of, any 20 or more of, any 21 or more of, any 22 or more of, any 23 or more of, any 24 or more of, or all 26 or more of outcomes (a)-(y) described immediately above.

Parameters (a)-(y) can be measured in accordance with any clinically acceptable methodology. For example, triglycerides, total cholesterol, HDL-C and fasting blood sugar can be sample from serum and analyzed using standard photometry techniques. VLDL-TG, LDL-C and VLDL-C can be calculated or determined using serum lipoprotein fractionation by preparative ultracentrifugation and subsequent quantitative analysis by refractometry or by analytic ultracentrifugal methodology. Apo A1, Apo B and hsCRP can be determined from serum using standard nephelometry techniques. Lipoprotein (a) can be determined from serum using standard turbidimetric immunoassay techniques. LDL particle number and particle size can be determined using nuclear magnetic resonance (NMR) spectrometry. Remnants lipoproteins and LDL-phospholipase A2 can be determined from EDTA plasma or serum and serum, respectively, using enzymatic immunoseparation techniques. Oxidized LDL, intercellular adhesion molecule-1 and interleukin-6 levels can be determined from serum using standard enzyme immunoassay techniques. These techniques are described in detail in standard textbooks, for example Tietz Fundamentals of Clinical Chemistry, $6^{th}$ Ed. (Burtis, Ashwood and Borter Eds.), WB Saunders Company.

In one embodiment, subjects fast for up to 12 hours prior to blood sample collection, for example about 10 hours.

In another embodiment, the present invention provides a method of treating or preventing primary hypercholesterolemia and/or mixed dyslipidemia (Fredrickson Types IIa and IIb) in a patient in need thereof, comprising administering to the patient one or more compositions as disclosed herein. In a related embodiment, the present invention provides a method of reducing triglyceride levels in a subject or subjects when treatment with a statin or niacin extended-release monotherapy is considered inadequate (Frederickson type IV hyperlipidemia).

In another embodiment, the present invention provides a method of treating or preventing risk of recurrent nonfatal myocardial infarction in a patient with a history of myocardial infarction, comprising administering to the patient one or more compositions as disclosed herein.

In another embodiment, the present invention provides a method of slowing progression of or promoting regression of atherosclerotic disease in a patient in need thereof, comprising administering to a subject in need thereof one or more compositions as disclosed herein.

In another embodiment, the present invention provides a method of treating or preventing very high serum triglyceride levels (e.g. Types IV and V hyperlipidemia) in a patient in need thereof, comprising administering to the patient one or more compositions as disclosed herein.

In another embodiment, the present invention provides a method of treating subjects having very high serum triglyceride levels (e.g. greater than 1000 mg/dl or greater than 2000 mg/dl) and that are at risk of developing pancreatitis, comprising administering to the patient one or more compositions as disclosed herein.

In one embodiment, a composition of the invention is administered to a subject in an amount sufficient to provide a daily dose of eicosapentaenoic acid of about 1 mg to about 10,000 mg, 25 about 5000 mg, about 50 to about 3000 mg, about 75 mg to about 2500 mg, or about 100 mg to about 1000 mg, for example about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg or about 2500 mg.

In another embodiment, any of the methods disclosed herein are used in treatment or prevention of a subject or subjects that consume a traditional Western diet. In one embodiment, the methods of the invention include a step of identifying a subject as a Western diet consumer or prudent diet consumer and then treating the subject if the subject is deemed a Western diet consumer. The term "Western diet" herein refers generally to a typical diet consisting of, by percentage of total calories, about 45% to about 50% carbohydrate, about 35% to about 40% fat, and about 10% to about 15% protein. A Western diet may alternately or additionally be characterized by relatively high intakes of red and processed meats, sweets, refined grains, and desserts, for example more than 50%, more than 60% or more or 70% of total calories come from these sources.

In one embodiment, a composition for use in methods of the invention comprises eicosapentaenoic acid, or a pharmaceutically acceptable ester, derivative, conjugate or salt thereof, or mixtures of any of the foregoing, collectively referred to herein as "EPA." The term "pharmaceutically acceptable" in the present context means that the substance in question does not produce unacceptable toxicity to the subject or interaction with other components of the composition.

In one embodiment, the EPA comprises all-cis eicosa-5,8,11,14,17-pentaenoic acid. In another embodiment, the EPA comprises an eicosapentaenoic acid ester. In another embodiment, the EPA comprises a $C_1$-$C_5$ alkyl ester of eicosapentaenoic acid. In another embodiment, the EPA comprises eicosapentaenoic acid ethyl ester, eicosapentaenoic acid methyl ester, eicosapentaenoic acid propyl ester, or eicosapentaenoic acid butyl ester. In another embodiment, the EPA comprises In one embodiment, the EPA comprises all-cis eicosa-5,8,11,14,17-pentaenoic acid ethyl ester.

In another embodiment, the EPA is in the form of ethyl-EPA, lithium EPA, mono-, di- or triglyceride EPA or any other ester or salt of EPA, or the free acid form of EPA. The EPA may also be in the form of a 2-substituted derivative or other derivative which slows down its rate of oxidation but does not otherwise change its biological action to any substantial degree.

In another embodiment, EPA is present in a composition useful in accordance with methods of the invention in an amount of about 50 mg to about 5000 mg, about 75 mg to about 2500 mg, or about 100 mg to about 1000 mg, for example about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg or about 2500 mg.

In another embodiment, a composition useful in accordance with the invention contains not more than about 10%, not more than about 9%, not more than about 8%, not more than about 7%, not more than about 6%, not more than about 5%, not more than about 4%, not more than about 3%, not more than about 2%, not more than about 1%, or not more than about 0.5%, by weight, docosahexaenoic acid (DHA), if any. In another embodiment, a composition of the invention contains substantially no docosahexaenoic acid. In still another embodiment, a composition useful in the present invention contains no docosahexaenoic acid and/or derivative thereof.

In another embodiment, EPA comprises at least 70%, at least 80%, at least 90%, at least 95%, at least 96%, at least 97%, at least 98%, at least 99%, or 100%, by weight, of all fatty acids present in a composition that is useful in methods of the present invention.

In one embodiment, a composition of the invention comprises ultra-pure EPA. The term "ultra-pure" as used herein with respect to EPA refers to a composition comprising at least 95% by weight EPA (as the term "EPA" is defined and exemplified herein). Ultra-pure EPA comprises at least 96% by weight EPA, at least 97% by weight EPA, or at least 98% by weight EPA, wherein the EPA is any form of EPA as set forth herein.

In another embodiment, a composition useful in accordance with methods of the invention contains less than 10%, less than 9%, less than 8%, less than 7%, less than 6%, less than 5%, less than 4%, less than 3%, less than 2%, less than 1%, less than 0.5% or less than 0.25%, by weight of the total composition or by weight of the total fatty acid content, of any fatty acid other than EPA. Illustrative examples of a "fatty acid other than EPA" include linolenic acid (LA), arachidonic acid (AA), docosahexaenoic acid (DHA), alpha-linolenic acid (ALA), stearadonic acid (STA), eicosatrienoic acid (ETA) and/or docosapentaenoic acid (DPA). In another embodiment, a composition useful in accordance with methods of the invention contains about 0.1% to about 4%, about 0.5% to about 3%, or about 1% to about 2%, by weight, of total fatty acids other than EPA and/or DHA.

In another embodiment, a composition useful in accordance with the invention has one or more of the following features: (a) eicosapentaenoic acid ethyl ester represents at least about 96%, at least about 97%, or at least about 98%, by weight, of all fatty acids present in the composition; (b) the composition contains not more than about 4%, not more than about 3%, or not more than about 2%, by weight, of total fatty acids other than eicosapentaenoic acid ethyl ester; (c) the composition contains not more than about 0.6%, not more than about 0.5%, or not more than about 0.4% of any individual fatty acid other than eicosapentaenoic acid ethyl ester; (d) the composition has a refractive index (20° C.) of about 1 to about 2, about 1.2 to about 1.8 or about 1.4 to about 1.5; (e) the composition has a specific gravity (20° C.) of about 0.8 to about 1.0, about 0.85 to about 0.95 or about 0.9 to about 0.92; (e) the composition contains not more than about 20 ppm, not more than about 15 ppm or not more than about 10 ppm heavy metals, (f) the composition contains not more than about 5 ppm, not more than about 4 ppm, not more than about 3 ppm, or not more than about 2 ppm arsenic, and/or (g) the composition has a peroxide value of not more than about 5 meq/kg, not more than about 4 meq/kg, not more than about 3 meq/kg, or not more than about 2 meq/kg.

In another embodiment, a composition useful in accordance with the invention comprises, consists of or consists essentially of at least 95% by weight ethyl eicosapentaenoate (EPA-E), about 0.2% to about 0.5% by weight ethyl octadecatetraenoate (ODTA-E), about 0.05% to about 0.25% by weight ethyl nonaecapentaenoate (NDPA-E), about 0.2% to about 0.45% by weight ethyl arachidonate (AA-E), about 0.3% to about 0.5% by weight ethyl eicosatetraenoate (ETA-E), and about 0.05% to about 0.32% ethyl heneicosapentaenoate (HPA-E). In another embodiment, the composition is present in a capsule shell.

In another embodiment, compositions useful in accordance with the invention comprise, consist essential of, or consist of at least 95%, 96% or 97%, by weight, ethyl eicosapentaenoate, about 0.2% to about 0.5% by weight ethyl octadecatetraenoate, about 0.05% to about 0.25% by weight ethyl nonaecapentaenoate, about 0.2% to about 0.45% by weight ethyl arachidonate, about 0.3% to about 0.5% by weight ethyl eicosatetraenoate, and about 0.05% to about 0.32% ethyl heneicosapentaenoate. Optionally, the composition contains not more than about 0.06%, about 0.05%, or about 0.04%, by weight, DHA or derivative there of such as ethyl-DHA. In one embodiment the composition contains substantially no or no amount of DHA or derivative there of such as ethyl-DHA. The composition further optionally comprises one or more antioxidants (e.g. tocopherol) or other impurities in an amount of not more than about 0.5% or not more than 0.05%. In another embodiment, the composition comprises about 0.05% to about 0.4%, for example about 0.2% by weight tocopherol. In another embodiment, about 500 mg to about 1 g of the composition is provided in a capsule shell.

In another embodiment, compositions useful in accordance with the invention comprise, consist essential of, or consist of at least 96% by weight ethyl eicosapentaenoate, about 0.22% to about 0.4% by weight ethyl octadecatetraenoate, about 0.075% to about 0.20% by weight ethyl nonaecapentaenoate, about 0.25% to about 0.40% by weight ethyl arachidonate, about 0.3% to about 0.4% by weight ethyl eicosatetraenoate and about 0.075% to about 0.25% ethyl heneicosapentaenoate. Optionally, the composition contains not more than about 0.06%, about 0.05%, or about 0.04%, by weight, DHA or derivative there of such as ethyl-DHA. In one embodiment the composition contains substantially no or no amount of DHA or derivative there of such as ethyl-DHA.

The composition further optionally comprises one or more antioxidants (e.g. tocopherol) or other impurities in an amount of not more than about 0.5% or not more than 0.05%. In another embodiment, the composition comprises about 0.05% to about 0.4%, for example about 0.2% by weight tocopherol. In another embodiment, the invention provides a dosage form comprising about 500 mg to about 1 g of the foregoing composition in a capsule shell. In one embodiment, the dosage form is a gel or liquid capsule and is packaged in blister packages of about 1 to about 20 capsules per sheet.

In another embodiment, compositions useful in accordance with the invention comprise, consist essential of, or consist of at least 96%, 97% or 98%, by weight, ethyl eicosapentaenoate, about 0.25% to about 0.38% by weight ethyl octadecatetraenoate, about 0.10% to about 0.15% by weight ethyl nonaecapentaenoate, about 0.25% to about 0.35% by weight ethyl arachidonate, about 0.31% to about 0.38% by weight ethyl eicosatetraenoate, and about 0.08% to about 0.20% ethyl heneicosapentaenoate. Optionally, the composition contains not more than about 0.06%, about 0.05%, or about 0.04%, by weight, DHA or derivative there of such as ethyl-DHA. In one embodiment the composition contains substantially no or no amount of DHA or derivative there of such as ethyl-DHA. The composition further optionally comprises one or more antioxidants (e.g. tocopherol) or other impurities in an amount of not more than about 0.5% or not more than 0.05%. In another embodiment, the composition comprises about 0.05% to about 0.4%, for example about 0.2% by weight tocopherol. In another embodiment, the invention provides a dosage form comprising about 500 mg to about 1 g of the foregoing composition in a capsule shell.

In another embodiment, a composition as described herein is administered to a subject once or twice per day. In another embodiment, 1, 2, 3 or 4 capsules, each containing about 1 g of a composition as described herein, are administered to a subject daily. In another embodiment, 1 or 2 capsules, each containing about 1 g of a composition as described herein, are administered to the subject in the morning, for example between about 5 am and about 11 am, and 1 or 2 capsules, each containing about 1 g of a composition as described herein, are administered to the subject in the evening, for example between about 5 pm and about 11 pm.

In one embodiment, a subject being treated in accordance with methods of the invention is not otherwise on lipid-altering therapy, for example statin, fibrate, niacin and/or ezetimibe therapy.

In another embodiment, compositions useful in accordance with methods of the invention are orally deliverable. The terms "orally deliverable" or "oral administration" herein include any form of delivery of a therapeutic agent or a composition thereof to a subject wherein the agent or composition is placed in the mouth of the subject, whether or not the agent or composition is swallowed. Thus "oral administration" includes buccal and sublingual as well as esophageal administration. In one embodiment, the composition is present in a capsule, for example a soft gelatin capsule.

A composition for use in accordance with the invention can be formulated as one or more dosage units. The terms "dose unit" and "dosage unit" herein refer to a portion of a pharmaceutical composition that contains an amount of a therapeutic agent suitable for a single administration to provide a therapeutic effect. Such dosage units may be administered one to a plurality (i.e. 1 to about 10, 1 to 8, 1 to 6, 1 to 4 or 1 to 2) of times per day, or as many times as needed to elicit a therapeutic response.

In another embodiment, the invention provides use of any composition described herein for treating moderate to severe hypertriglyceridemia in a subject in need thereof, comprising: providing a subject having a fasting baseline triglyceride level of about 500 mg/dl to about 1500 mg/dl and administering to the subject a pharmaceutical composition as described herein. In one embodiment, the composition comprises about 1 g to about 4 g of eicosapentaenoic acid ethyl ester, wherein the composition contains substantially no docosahexaenoic acid.

In one embodiment, compositions of the invention, upon storage in a closed container maintained at room temperature, refrigerated (e.g. about 5 to about 5 -10° C.) temperature, or frozen for a period of about 1, 2, 3, 4, 5, 6, 7, 8, 9, 10, 11, or 12 months, exhibit at least about 90%, at least about 95%, at least about 97.5%, or at least about 99% of the active ingredient(s) originally present therein.

In one embodiment, the invention provides use of a composition as described herein in manufacture of a medicament for treatment of any of a cardiovascular-related disease. In another embodiment, the subject is diabetic.

In one embodiment, a composition as set forth herein is packaged together with instructions for using the composition to treat a cardiovascular disorder.

EXAMPLES

A multi-center, placebo-controlled randomized, double-blind, 12-week study with an open-label extension is performed to evaluate the efficacy and safety of AMR101 in patients with fasting triglyceride levels $\geqq$500 mg/dL. The primary objective of the study is to determine the efficacy of AMR101 2 g daily and 4 g daily, compared to placebo, in lowering fasting TG levels in patients with fasting TG levels $\geqq$500 mg/dL and $\leqq$1500 mg/dL ($\geqq$5.65 mmol/L and $\leqq$16.94 mmol/L).

The secondary objectives of this study are the following:
1. To determine the safety and tolerability of AMR101 2 g daily and 4 g daily;
2. To determine the effect of AMR101 on lipid and apolipoprotein profiles;
3. To determine the effect of AMR101 on low-density lipoprotein (LDL) particle number and size;
4. To determine the effect of AMR101 on oxidized LDL;
5. To determine the effect of AMR101 on fasting plasma glucose (FPG) and hemoglobin $A_{1c}$ (Hb$A_{1c}$);
6. To determine the effect of AMR101 on insulin resistance;
7. To determine the effect of AMR101 on high-sensitivity C-reactive protein (hsCRP);
8. To determine the effects of AMR101 2 g daily and 4 g daily on the incorporation of fatty acids into red blood cell membranes and into plasma phospholipids;
9. To explore the relationship between baseline fasting TG levels and the reduction in fasting TG levels; and
10. To explore the relationship between an increase in red blood cell membrane eicosapentaenoic acid (EPA) concentrations and the reduction in fasting TG levels.

The population for this study is men and women (women of childbearing potential will need to be on contraception or practice abstinence) >18 years of age with a body mass index $\leqq$45 kg/m$^2$ who are not on lipid-altering therapy or are currently on lipid-altering therapy. Patients currently on statin therapy (with or without ezetimibe) will be evaluated by the investigator as to whether this therapy can be safely discontinued at screening, or if it should be continued. If statin therapy (with or without ezetimibe) is to be continued, dose(s) must be stable for $\geqq$4 weeks prior to randomization. Patients taking non-statin, lipid-altering medications (niacin >200 mg/day, fibrates, fish oil, other products containing omega-3 fatty acids, or other herbal products or dietary supplements with potential lipid-altering effects), either alone or in combination with statin therapy (with or without ezetimibe), must be able to safely discontinue non-statin, lipid-altering therapy at screening.

Approximately 240 patients will be randomized at approximately 50 centers in North America, South America, Central America, Europe, India, and South Africa. The study will be a 58- to 60-week, Phase 3, multi-center study consisting of 3 study periods: (1) A 6- to 8-week screening period that includes a diet and lifestyle stabilization and washout period and a TG qualifying period; (2) A 12-week, double-blind, randomized, placebo-controlled treatment period; and (3) A 40-week, open-label, extension period.

During the screening period and double-blind treatment period, all visits are to be within ±3 days of the scheduled time. During the open-label extension period, all visits are to be within ±7 days of the scheduled time. The screening period includes a 4- or 6-week diet and lifestyle stabilization period and washout period followed by a 2-week TG qualifying period. s) must be stable for $\geqq$4 weeks prior to randomization.

The screening visit (Visit 1) will occur for all patients at either 6 weeks (for patients not on lipid-altering therapy at screening or for patients who will not need to discontinue their current lipid-altering therapy) or 8 weeks (for patients who will require washout of their current lipid-altering therapy at screening) before randomization, as follows:

Patients who do not require a washout: The screening visit will occur at Visit 1 (Week −6). Eligible patients will enter a 4-week diet and lifestyle stabilization period. At the screening visit, all patients will receive counseling regarding the importance of the National Cholesterol Education Program (NCEP) Therapeutic Lifestyle Changes (TLC) diet and will receive instructions on how to follow this diet. Patients who will require a washout: The screening visit will occur at Visit 1 (Week −8). Eligible patients will begin a 6-week washout period at the screening visit. Patients will receive counseling regarding the NCEP TLC diet and will receive instructions on how to follow this diet. Site personnel will contact patients who do not qualify for participation based on screening laboratory test results to instruct them to resume their prior lipid-altering medications.

At the end of the 4-week diet and lifestyle stabilization period or the 6-week diet and stabilization and washout period, eligible patients will enter the 2-week TG qualifying period and will have their fasting TG level measured at Visit 2 (Week −2) and Visit 3 (Week −1). Eligible patients must have an average fasting TG level $\geqq$500 mg/dL and $\leqq$1500 mg/dL ($\geqq$5.65 mmol/L and $\leqq$16.94 mmol/L) to enter the 12-week double-blind treatment period. The TG level for qualification will be based on the average (arithmetic mean) of the Visit 2 (Week −2) and Visit 3 (Week −1) values. If a patient's average TG level from Visit 2 and Visit 3 falls outside the required range for entry into the study, an additional sample for fasting TG measurement can be collected 1 week later at Visit 3.1. If a third sample is collected at Visit 3.1, entry into the study will be based on the average (arithmetic mean) of the values from Visit 3 and Visit 3.1.

After confirmation of qualifying fasting TG values, eligible patients will enter a 12-week, randomized, double-blind treatment period. At Visit 4 (Week 0), patients will be randomly assigned to 1 of the following treatment groups:
AMR101 2 g daily,
AMR101 4 g daily, or
Placebo.

During the double-blind treatment period, patients will return to the site at Visit 5 (Week 4), Visit 6 (Week 11), and Visit 7 (Week 12) for efficacy and safety evaluations.

Patients who complete the 12-week double-blind treatment period will be eligible to enter a 40-week, open-label, extension period at Visit 7 (Week 12). All patients will receive open-label AMR101 4 g daily. From Visit 8 (Week 16) until the end of the study, changes to the lipid-altering regimen are permitted (e.g., initiating or raising the dose of statin or adding non-statin, lipid-altering medications to the regimen), as guided by standard practice and prescribing information. After Visit 8 (Week 16), patients will return to the site every 12 weeks until the last visit at Visit 11 (Week 52).

Eligible patients will be randomly assigned at Visit 4 (Week 0) to receive orally AMR101 2 g daily, AMR101 4 g daily, or placebo for the 12-week double-blind treatment period. AMR101 is provided in 1 g liquid-filled, oblong, gelatin capsules. The matching placebo capsule is filled with light liquid paraffin and contains 0 g of AMR101. During the double-blind treatment period, patients will take 2 capsules (AMR101 or matching placebo) in the morning and 2 in the evening for a total of 4 capsules per day. Patients in the AMR101 2 g/day treatment group will receive 1 AMR101 1 g capsule and 1 matching placebo capsule in the morning and in the evening. Patients in the AMR101 4 g/day treatment group will receive 2 AMR101 1 g capsules in the morning and evening.

Patients in the placebo group will receive 2 matching placebo capsules in the morning and evening. During the extension period, patients will receive open-label AMR101 4 g daily. Patients will take 2 AMR101 1 g capsules in the morning and 2 in the evening.

The primary efficacy variable for the double-blind treatment period is percent change in TG from baseline to Week 12 endpoint. The secondary efficacy variables for the double-blind treatment period include the following:

Percent changes in total cholesterol (TC), high-density lipoprotein cholesterol (HDL-C), calculated low-density lipoprotein cholesterol (LDL-C), calculated non-high-density lipoprotein cholesterol (non-HDL-C), and very low-density lipoprotein cholesterol (VLDL-C) from baseline to Week 12 endpoint;

Percent change in very low-density lipoprotein TG from baseline to Week 12;

Percent changes in apolipoprotein A-I (apo A-I), apolipoprotein B (apo B), and apo A-I/apo B ratio from baseline to Week 12;

Percent changes in lipoprotein(a) from baseline to Week 12 (selected sites only);

Percent changes in LDL particle number and size, measured by nuclear magnetic resonance, from baseline to Week 12 (selected sites only);

Percent change in remnant-like particle cholesterol from baseline to Week 12 (selected sites only);

Percent change in oxidized LDL from baseline to Week 12 (selected sites only);

Changes in FPG and $HbA_{1c}$ from baseline to Week 12;

Change in insulin resistance, as assessed by the homeostasis model index insulin resistance, from baseline to Week 12;

Percent change in lipoprotein associated phospholipase A2 from baseline to Week 12 (selected sites only);

Change in intracellular adhesion molecule-1 from baseline to Week 12 (selected sites only);

Change in interleukin-6 from baseline to Week 12 (selected sites only);

Change in plasminogen activator inhibitor-1 from baseline to Week 12 (selected sites only);

Change in hsCRP from baseline to Week 12 (selected sites only);

Change in serum phospholipid EPA content from baseline to Week 12;

Change in red blood cell membrane EPA content from baseline to Week 12; and

Change in serum phospholipid and red blood cell membrane content in the following fatty acids from baseline to Week 12: docosapentaenoic acid, docosahexaenoic acid, arachidonic acid, palmitic acid, stearic acid, and oleic acid.

The efficacy variable for the open-label extension period is percent change in fasting TG from extension baseline to end of treatment. Safety assessments will include adverse events, clinical laboratory measurements (chemistry, hematology, and urinalysis), 12-lead electrocardiograms (ECGs), vital signs, and physical examinations For TG, TC, HDL-C, calculated LDL-C, calculated non-HDL-C, and VLDL-C, baseline will be defined as the average of Visit 4 (Week 0) and the preceding lipid qualifying visit (either Visit 3 [Week −1] or if it occurs, Visit 3.1) measurements. Baseline for all other efficacy parameters will be the Visit 4 (Week 0) measurement.

For TC, HDL-C, calculated LDL-C, calculated non-HDL-C, and VLDL-C, Week 12 endpoint will be defined as the average of Visit 6 (Week 11) and Visit 7 (Week 12) measurements. Week 12 endpoint for all other efficacy parameters will be the Visit 7 (Week 12) measurement.

The primary efficacy analysis will be performed using a 2-way analysis of covariance (ANCOVA) model with treatment as a factor and baseline TG value as a covariate. The least-squares mean, standard error, and 2-tailed 95% confidence interval for each treatment group and for each comparison will be estimated. The same 2-way ANCOVA model will be used for the analysis of secondary efficacy variables.

The primary analysis will be repeated for the per-protocol population to confirm the robustness of the results for the intent-to-treat population.

The primary efficacy variable will be the percent change in fasting TG levels from baseline to Week 12. A sample size of 69 completed patients per treatment group will provide ≧90% power to detect a difference of 30% between AMR101 and placebo in percent change from baseline in fasting TG levels, assuming a standard deviation of 45% in TG measurements and a significance level of p<0.01. To accommodate a 15% drop-out rate from randomization to completion of the double-blind treatment period, a total of 240 randomized patients is planned (80 patients per treatment group).

What is claimed is:

1. A method of reducing triglycerides and apolipoprotein B in a subject having a fasting baseline triglyceride level of 500 mg/dl to about 1500 mg/dl, who does not receive a concurrent lipid altering therapy, comprising administering orally to the subject about 4 g per day of a pharmaceutical composition comprising at least about 96% by weight, ethyl eicosapentaenoate (ethyl-EPA) and substantially no docosahexaenoic acid (DHA) or its esters for a period of at least 12 weeks to effect a reduction in triglycerides and apolipoprotein B in the subject compared to a triglyceride level and apolipoprotein B level in a second subject having a fasting baseline triglyceride level of 500 mg/dl to about 1500 mg/dl, who does not receive a concurrent lipid altering therapy, and who has not received the pharmaceutical composition.

2. The method of claim 1 wherein the composition is administered to the subject 1 to 4 times per day.

3. The method of claim 1 wherein the composition is present in one or more capsules.

4. The method of claim 1 comprising administering the composition to the subject daily for a period of 12 weeks to effect a reduction in apolipoprotein B and substantially no increase in LDL-C levels compared to the second subject.

5. The method of claim 1 comprising administering 4 g of the composition to the subject daily for a period of 12 weeks to effect at least a 5% reduction in triglyceride levels compared to a triglyceride level in the second subject.

6. The method of claim 1 comprising administering 4 g of the composition to the subject daily for a period of 12 weeks to effect at least a 5% reduction in VLDL-C levels compared to a VLDL-C level in the second subject.

7. The method of claim 1 comprising administering 4 g of the composition to the subject daily for a period of 12 weeks to effect a reduction in non-HDL-C levels compared to a non-HDL-C level in the second subject.

8. The method of claim 1 comprising administering 4 g of the composition to the subject daily for a period of 12 weeks to effect a reduction in triglycerides of at least about 25% and a reduction in non-HDL C of at least about 5% as compared to the second subject.

9. The method of claim 1 comprising administering 4 g of the composition to the subject daily for a period of 12 weeks to effect a reduction in Lp-PLA2 of at least about 15% as compared a Lp-PLA2 level in the second subject.

10. The method of claim 9 comprising administering 4 g of the composition to the subject daily for a period of 12 weeks to effect a reduction in total cholesterol of at least about 15% as compared a total cholesterol level in the second subject.

11. The method of claim 1 wherein the subject and the second subject consume a Western diet.

12. The method of claim 1 wherein the concomitant lipid-altering therapy is a statin.

13. A method of reducing triglycerides in a subject having a fasting baseline triglyceride level of 500 mg/dl to about 1500 mg/dl, who does not receive a concurrent lipid altering therapy, comprising administering orally to the subject about 4 g per day of a pharmaceutical composition comprising at least about 96% by weight, ethyl eicosapentaenoate (ethyl-EPA) and substantially no docosahexaenoic acid (DHA) or its esters for a period of at least 12 weeks to effect a statistically significant reduction in triglycerides without effecting a statistically significant increase in LDL-C or apolipoprotein B in the subject.

14. The method of claim 13 comprising administering to the subject about 4 g per day of the pharmaceutical composition to effect a statistically significant reduction in triglycerides and apolipoprotein B without effecting a statistically significant increase of in the subject.

15. The method of claim 13 wherein the subject and the second subject consume a Western diet.

16. The method of claim 13 wherein the concomitant lipid-altering therapy is a statin.

17. A method of reducing triglycerides and apolipoprotein B in a subject having a fasting baseline triglyceride level of 500 mg/dl to about 1500 mg/dl, who does not receive a concurrent lipid altering therapy, comprising administering orally to the subject about 4 g per day of a pharmaceutical composition comprising at least about 96% by weight, ethyl eicosapentaenoate (ethyl-EPA) and substantially no docosahexaenoic acid (DHA) or its esters for a period of at least 12 weeks to effect reduction in triglycerides and apolipoprotein B in the subject compared to a triglyceride level and an apolipoprotein B level at a baseline prior to initial administration of the pharmaceutical composition.

18. The method of claim 17 wherein the subject and the second subject consume a Western diet.

19. The method of claim 17 wherein the concomitant lipid-altering therapy is a statin.

* * * * *

UNITED STATES PATENT AND TRADEMARK OFFICE
CERTIFICATE OF CORRECTION

PATENT NO.        : 8,318,715 B2
APPLICATION NO.   : 13/282145
DATED             : November 27, 2012
INVENTOR(S)       : Manku et al.

It is certified that error appears in the above-identified patent and that said Letters Patent is hereby corrected as shown below:

In the Claims

Column 18, line 16, of Claim 14, should read, "...significant increase of LDL-C in the subject."

Column 18, lines 17-18, of Claim 15, should read, "The method of claim 13 wherein the subject consumes a Western Diet."

Signed and Sealed this
Eleventh Day of August, 2015

Michelle K. Lee
*Director of the United States Patent and Trademark Office*